(12) United States Patent
Curran et al.

(10) Patent No.: US 6,806,357 B1
(45) Date of Patent: Oct. 19, 2004

(54) FLUOROUS NUCLEOPHILIC SUBSTITUTION OF ALCOHOLS AND REAGENTS FOR USE THEREIN

(75) Inventors: Dennis P. Curran, Pittsburgh, PA (US); Sivaraman Dandapani, Pittsburgh, PA (US)

(73) Assignee: University of Pittsburgh, Pittsburgh, PA (US)

( * ) Notice: Subject to any disclaimer, the term of this patent is extended or adjusted under 35 U.S.C. 154(b) by 0 days.

(21) Appl. No.: 09/932,903

(22) Filed: Aug. 20, 2001

(51) Int. Cl.[7] .................. C07C 245/00; C07C 67/36
(52) U.S. Cl. .................. 534/558; 560/115; 560/114; 560/8
(58) Field of Search .................. 534/558; 560/115, 560/114, 8

(56) References Cited

U.S. PATENT DOCUMENTS

| | | | |
|---|---|---|---|
| 5,463,082 A | 7/1993 | Horvath | |
| 5,777,121 A | 6/1996 | Curran | |
| 5,859,247 A | 7/1996 | Curran | |
| 6,156,896 A | 7/1996 | Curran | |

FOREIGN PATENT DOCUMENTS

| | | | |
|---|---|---|---|
| WO | WO 97/35199 | * | 9/1997 |
| WO | WO 97/351199 | * | 9/1997 |
| WO | WO 03/016246 | | 2/2003 |

OTHER PUBLICATIONS

Tunoori, A. R.; Dutta, D.; Georg, G.I. "Polymer–bound triphenylphosphine as traceless reagent for Mitsunobu reactions in combinatorial chemistry: Synthesis of aryl ethers from phenols and alcohols" Tetrahedron Lett. 1998, 39, 8751–8754.

Amold, L.D.; Assil, H. I.; Vederas, J. "Polymer–Supported Alkyl Azodicarboxylates for Mitsunobu Reactions" J. Am. Chem. Soc. 1989, 111, 3973–76.

Starkey, G.W.; Parlow, J. J.; Flynn, D.L. "Chemically–Tagged Misunobu Reagents for Use in Solution Phase Chemical Library Synthesis" Bioorg. Med. Chem. Lett. 1998, 8, 2385–89.

Danielson, N.D. et al., "Fluropolymers and Flurocarbon Bonded Phases as Column Packings for Liquid Chromatography," J. Chromat., 544, 187–199 (1991).

Kainz, S., Luo, Z.Y., Curran, D.P. Leitner, W., "Synthesis of Perfluoroalkyl–Substituted Aryl Bromides and Thier Purification over Fluorous Reverse phase Silica", Synthesis, 1425–1427 (1998).

Curran, D.P., Halida, S., HE, M., "ThermalAllylations of Aldehydes with a Fluorous Allylstannane. Separation of Organic and Fluorous Productions by Solid Phase Extraction with Fluorous Reverse Phase Silica Gel", J. Org. Chem., 62, 6714–6715 (1997).

Bhattacharyya P. et al.; Phosphorus (III) Ligands with Florous Ponytails; Journal Chem. Soc., Letchworth, GB; 1997, 3609–3612.

Barrett, A. G. M.; Roberts, R. S.; Schroder, J. "Impurity annihilation: Chromatography–free parallel Mitsunobu reactions" Org Lett 2000, 2, 2999–3001.

Curran, D. P. "Parallel Synthesis with Fluorous Reagents and Reactants" Med. Res. Rev. 1999, 19, 432–438.

Curran, D. P. "Strategy–level separations in organic synthesis: From planning to practice" Angew. Chem., Int. Ed. Eng. 1998, 37, 1175–1196.

Curran, D. P.; Luo, Z. Y. "Fluorous synthesis with fewer fluorines (Light fluorous synthesis): separation of tagged from untagged products by solid–phase extraction with fluorous reverse–phase silica gel" J. Am. Chem. Soc. 1999, 121, 9069–9072.

* cited by examiner

*Primary Examiner*—Rita Desai
*Assistant Examiner*—Hector M Reyes
(74) *Attorney, Agent, or Firm*—Bartony & Hare, LLP

(57) ABSTRACT

A method of effecting a nucleophilic substitution of an alcohol to produce a target product includes the steps of:

reacting the alcohol and a nucleophile with an azodicarboxylate and a phosphine. At least one of the azodicarboxylate and the phosphine includes at least one fluorous tag. In several embodiments, the azodicarboxylate includes at least one fluorous tag, and the phosphine includes at least one fluorous tag. A compound has the formula:

$Z^1O_2C-N=N-CO_2Z^2$, wherein $Z^1$ is

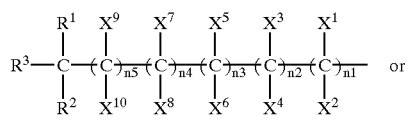

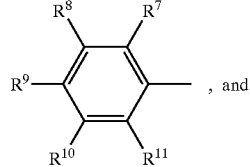

, and $Z^2$ is

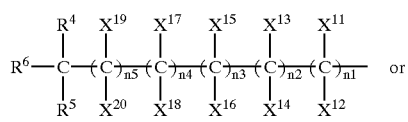

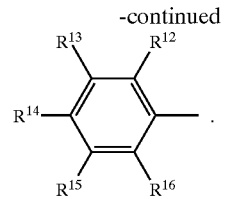

In the above formula n1, n2, n3, n4, n5, n6, n7, n8, n9 and n10 are independently 1 or 0. $X^1$, $X^2$, $X^3$, $X^4$, $X^5$, $X^6$, $X^7$, $X^8$, $X^9$, $X^{10}$, $X^{11}$, $X^{12}$, $X^{13}$, $X^{14}$, $X^{15}$, $X^{16}$, $X^{17}$, $X^{18}$, $X^{19}$ and $X^{20}$ are independently H, F, Cl, an alkyl group, an aryl group or an alkoxy group. $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$ and $R^{16}$ are independently H, F, Cl, an alkyl group, an alkoxy group, a thioalkyl group, a dialkylamino group, a nitro group, a cyano group, a perfluoroalkyl group, a hydrofluoroalkyl group, a fluorinated ether group, a fluorinated amine group, $O-Rf^1$, $S-Rf^2$, or $-N(Rf^3)(R^{22})$, wherein $R^{22}$ is an alkyl group or $Rf^4$, and wherein $Rf^1$, $Rf^2$, $Rf^3$ and $Rf^4$ are independently a fluorous group selected from the group of a perfluoroalkyl group, a hydrofluoroalkyl group, a fluorinated ether group or a fluorinated amine group. At least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$ or $R^{16}$ is $O-Rf^1$, $S-Rf^2$, $-N(Rf^3)(R^{22})$, a perfluoroalkyl group, a hydrofluoroalkyl group, a fluorinated ether group or a fluorinated amine group.

24 Claims, 10 Drawing Sheets

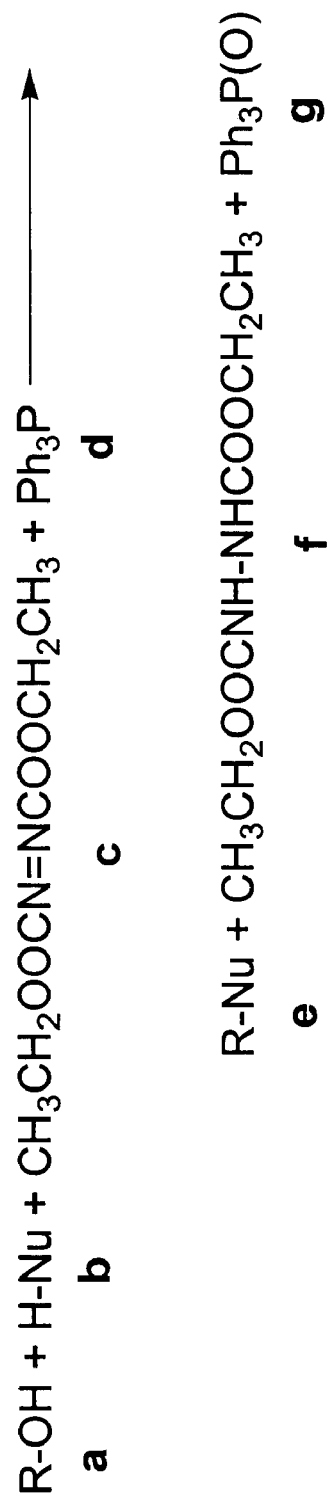
Figure 1 A Traditional Solution Phase Mitsunobu Reaction

FLUOROUS NUCLEOPHILIC SUBSTITUTION OF ALCOHOLS AND REAGENTS FOR USE THEREIN

BACKGROUND OF THE INVENTION

The present invention relates to nucleophilic substitution of alcohols, and, especially, to fluorous nucleophilic substitution of alcohols and fluorous reagents therefor.

References set forth herein may facilitate understanding of the present invention or the background of the present invention. Inclusion of a reference herein, however, is not intended to and does not constitute an admission that the reference is available as prior art with respect to the present invention.

The Mitsunobu reaction is one of the most popular and powerful reactions in organic, synthesis and its uses range from natural products synthesis to parallel synthesis and combinatorial chemistry. See, for example, Hughes, D. L. "Progress in the Mitsunobu reaction. A review." Org. Prep. Proced. Int. 1996, 28,–127–164; Hughes, D. L. "The Mitsunobu reaction." Org. React. (N.Y.) 1992; 42, 335–656; and Mitsunobu, O. "Synthesis of Alcohols and Ethers." in Comprehensive Organic Synthesis; Trost, B. M. and Fleming, I., Ed.; Pergamon Press: Oxford, 1991; Vol. 6; pp 1 32. The Mitsunobu reaction is so commonly used because it allows the one-step substitution of a primary or secondary alcohol by a nucleophile. Nucleophilic substitutions of alcohols are common synthetic transformations but other general methods require two or more steps.

A traditional solution phase Mitsunobu reaction as illustrated in FIG. 1 combines an alcohol a, an acidic pro-nucleophile b, diethylazodicarboxylate c (typically referred to as "DEAD") and triphenylphosphine d in an organic solvent such as dichloromethane or tetrahydrofuran (THF). The reagents and reactants can be combined in different orders according to several standard procedures. The products of the reaction are the desired substitution product e, the hydrazine f derived from the reduction of c and triphenylphosphine oxide g derived from the oxidation of d. If either reagent c or d is used in excess, then this unreacted reagent may also be present. The desired product of the reaction e is typically separated from the reagent byproducts and any excess reagents by chromatography.

The need for a careful chromatographic separation is a substantial limitation of the Mitsunobu reaction. The required separation is expensive on large scale. On small scale, the time and effort needed for multiple chromatographic separations limit combinatorial and parallel applications of the reaction.

Two general approaches have been. taken to facilitate separation in Mitsunobu reactions. First, both the phosphine and the azodicarboxylate have been attached to polymeric solid phases. See, for example, Tunoori, A. R.; Dutta, D.; Georg, G. I. "Polymer-Bound Triphenylphosphine as Traceless Reagent for Mitsunobu Reactions in Combinatorial Chemistry: Synthesis of Aryl Ethers from Phenols and Alcohols" Tetrahedron Lett. 1998, 39, 8751–8754; and Arnold, L. D.; Assil, H. I.; Vederas, J. "Polymer-Supported Alkyl Azodicarboxylates for Mitsunobu Reactions" J. Am. Chem. Soc. 1989, 111, 3973–3976. Polymer-bound reagents and reactants can be removed from final products by simple filtration. However, in the Mitsunobu reaction, the polymer approach only solves half the problem since the two polymer-bound reagents (azodicarboxylate and phosphine) cannot be used simultaneously. These reagents must react with each other and this reaction is blocked if both are bound to polymers. So only one polymer-bound reagent can be used and the other must be a soluble reagent.

In the second approach, soluble reagents are used and then these reagents are transformed by a chemical reaction after the Mitsunobu reaction is over. See, for example, Starkey, G. W.; Parlow, J. J.; Flynn, D. L. "Chemically-Tagged Mitsunobu Reagents for Use in Solution Phase Chemical Library Synthesis" *Bioorg. Med. Chem. Lett.*, 8, 2384–89 (1998). For example, soluble phosphine and azodicarboxylate reagents with suitable functionalities can be polymerized after a Mitsunobu reaction is over and then removed by filtration. This second approach is inefficient since it requires an extra chemical reaction (with associated reagents, time and effort, etc.) which contributes only to separation and not to formation of a desired product. In addition, the desired product cannot contain any functionality that would participate in the polymerization reaction. The second approach of facilitating separation thus imposes limitations that are not imposed by a normal Mitsunobu reaction.

It is very desirable to develop improved methods for nucleophilic substitution of alcohols and reagents thereofor to, for example, reduce or eliminate the above problems with current Mitsunobu reactions.

SUMMARY OF THE INVENTION

In one aspect, the present invention provides a method of effecting a nucleophilic substitution of an alcohol to produce a target product including the steps of: reacting the alcohol and a nucleophile with an azodicarboxylate and a phosphine. At least one of the azodicarboxylate and the phosphine including at least one fluorous tag. In several embodiments, the azodicarboxylate includes at least one fluorous tag, and the phosphine includes at least one fluorous tag.

The method preferably further includes the step of separating the target product from the fluorous tagged azodicarboxylate and/or the fluorous tagged phosphine via a fluorous separation technique. The fluorous separation technique can, for example be a liquid-liquid extraction. The fluorous separation technique can also be a solid-liquid extraction. The fluorous separation technique can also be a fluorous solid phase extraction or a fluorous chromatography.

The term "nucleophile" as used herein refers generally to an ion or a molecule that donates a pair of electrons to an atomic nucleus to form a covalent bond. Suitable nucleophiles for use in the present invention are conjugate bases of organic or inorganic acids. These acids should have a pKa preferably less than or equal to about 20, and more preferably less than or equal to about 15. Even more preferably, the pKa is less than or equal to about 12. The conjugate bases of many types of organic acids are known by those skilled in the art to be suitable for Mitsunobu reactions. Suitable nucleophiles include, but are not limited to, the conjugate bases derived from carboxylic acids, phenols, hydroxamic acids, imides, sulfonimides, sulfonamides, thiols, thioacids, thioamides, beta-dicarbonyls and assorted heterocycles. Nucleophilic conjugate bases derived from inorganic acids such as hydrogen halides or hydrogen azide, are also suitable.

Organic alcohols include a saturated carbon bonded to a hydroxyl group. Alcohols that participate in the Mitsunobu reaction are well known to those skilled in the art and include methanol and primary (for example, ethanol, propanol, allyl alcohol) and secondary (for example isopropanol and 1-phenylethanol) alcohols. Tertiary alcohols are less preferred but can still be used in some (especially intramolecular) applications.

The alcohol and the nucleophile can be in different molecules, or in the same molecule. In the later case (an intramolecular Mitsunobu reaction), a new ring is formed.

The fluorous tagged azodicarboxylate can, for example, have the formula:

$$Z^1O_2C-N=N-CO_2Z^2$$

wherein Z, is

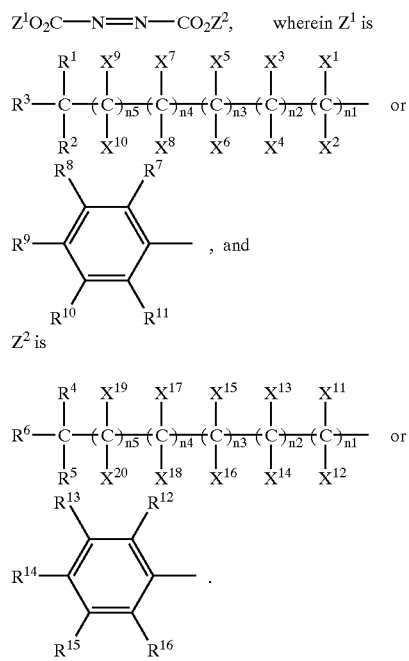

$Z^2$ is

In the above formula n1, n2, n3, n4, n5, n6, n7, n8, n9 and n10 are independently 1 or 0. $X^1, X^2, X^3, X^4, X^5, X^6, X^7, X^8, X^9, X^{10}, X^{11}, X^{12}, X^{13}, X^{14}, X^{15}, X^{16}, X^{17}, X^{18}, X^{19}$ and $X^{20}$ are independently H, F, Cl, an alkyl group, an aryl group or an alkoxy group. $R^1, R^2, R^3, R^4, R^5, R^6, R^7, R^8, R^9, R^{10}, R^{11}, R^{12}, R^{13}, R^{14}, R^{15}$ and $R^{16}$ are indenpendently H, F, Cl, an alkyl group, an alkoxy group, a thioalkyl group, a dialkylamino group, a nitro group, a cyano group, a perfluoroalkyl group, a hydrofluoroalkyl group, a fluorinated ether group, a fluorinated amine group, O—$Rf^1$, S—$Rf^2$, or —N($Rf^3$)($R^{22}$), wherein $R^{22}$ is an alkyl group or $Rf^4$, and wherein $Rf^1$, $Rf^2$, $Rf^3$ and $Rf^4$ are independently a fluorous group selected from the group of a perfluoroalkyl group, a hydrofluoroalkyl group, a fluorinated ether group, or a fluorinated amine group. At least one of $R^1, R^2, R^3, R^4, R^5, R^6, R^7, R^8, R^9, R^{10}, R^{11}, R^{12}, R^{13}, R^{14}, R^{15}$ or $R^{16}$ is O—$Rf^1$, S—$Rf^2$, —N($Rf^3$)($R^{22}$), a perfluoroalkyl group, a hydrofluoroalkyl group, a fluorinated ether group or a fluorinated amine group.

Perfluoroalkyl groups are preferably of 3 to 20 carbons. Hydrofluoroalkyl groups are preferably of 3 to 20 carbons and include up to one hydrogen atom for each two fluorine atoms. For example, perfluorinated ether groups can have the general formula —[(CF$_2$)$_x$O(CF$_2$)$_y$]$_z$CF$_3$, wherein x, y and z are integers. Perfluorinated amine groups can, for example, have the general formula —[(CF$_2$)$_{x'}$(NR$^a$)CF$_2$)$_{y'}$]$_{z'}$CF$_3$, wherein x', y' and z' are integers and wherein R$^a$ can, for example, be CF$_3$ or (CF$_2$)$_{n'}$CF$_3$ wherein n' is an integer. Fluorinated ether groups and fluorinated amine groups suitable for use in the present invention need not be perfluorinated, however. Fluorinated ether groups are preferably of 3 to 20 carbons. Fluorinated amine groups are preferably of 4 to 20 carbons.

The fluorous tagged phosphine can, for example, have the formula

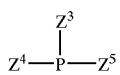

wherein $Z^3$ is

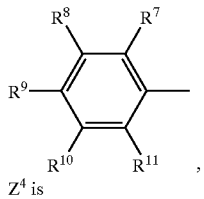

$Z^4$ is

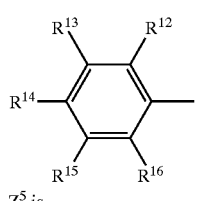

, and $Z^5$ is

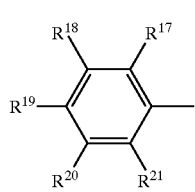

In the above formula $R^7, R^8, R^9, R^{10}, R^{11}, R^{12}, R^{13}, R^{14}, R^{15}$ and $R^{16}, R^{17}, R^{18}, R^{19}, R^{20}$, and $R^{21}$ are independently H, F, Cl, an alkyl group, an alkoxy group, a thioalkyl group, a dialkylamino group, a nitro group, a cyano group, a perfluoroalkyl group, a hydrofluoroalkyl group, a fluorinated ether group, a fluorinated arnine group, O—Rf$^1$, S—Rf$^2$, —N(Rf$^3$)(R$^{22}$), wherein R$^{22}$ is an alklyl group or Rf$^4$, and wherein Rf$^1$, Rf$^2$, Rf$^3$ and R$^4$ are independently a fluorous group selected from the group of a perfluoroalkyl group, a hydrofluoroalkyl group, a fluorinated ether group or a fluorinated amine group. At least one of $R^7, R^8, R^9, R^{10}, R^{11}, R^{12}, R^{13}, R^{14}, R^{15}, R^{16}, R^{17}, R^{18}, R^{19}, R^{20}$ and $R^{21}$ is O—Rf$^1$, S—Rf$^2$, —N(Rf$^3$)(R$^{22}$), perfluoroalkyl group, a hydrofluoroalkyl group, a fluorinated ether group or a fluorinated amine group.

Once again, perfluoroalkyl groups are preferably of 3 to 20 carbons and hydrofluoroalkyl groups are preferably of 3 to 20 carbons. Hydrofluoroalkyl groups preferably include up to one hydrogen atom for each two fluorine atoms.

The alcohol upon which a nucleophilic substitution is effected is preferably a primary alcohol or a secondary alcohol. The alcohol and the nucleophile can, for example, be added to a mixture of the fluorous tagged azodicarboxylate and the fluorous tagged phosphine.

In another aspect, the present invention provides a compound having the formula $$Z^1O_2C-N=N-CO_2Z^2$$

wherein $Z^1$ and $Z^2$ are as defined above.

In another aspect, the present invention provides a compound having the formula $$Z^1O_2C-\underset{H}{N}-\underset{H}{N}-CO_2Z^2$$

wherein $Z^1$ and $Z^2$ are as defined above.

In still a further aspect, the present invention provides a method of synthesizing a compound having the formula:

$$Z^1O_2C-N=N-CO_2Z^2$$

comprising the step reacting a compound having the formula:

$$Z^1O_2C-\underset{H}{N}-\underset{H}{N}-CO_2Z^2$$

(wherein $Z^1$ and $Z^2$ are as defined above) with an oxidant. In one embodiment, the oxidant is dibromine.

In several embodiments of the present invention $Z^1$ and $Z^2$ are $Rf(CH_2)_N-$, wherein N is an integer in the range of 1 to 5 and Rf is a perfluoroalkyl group. Preferably, the perfluoroalkyl group is of 3 to 20 carbons. In several embodiments, linear perfluoroalkyl groups of 3 to 20 carbons were present.

As used herein, the terms "product" or "target product" refer generally to the target or desired molecule(s) of the nucleophilic substitution of the substrate alcohol resulting from reaction of the substrate alcohol with the other reaction component(s) of the present invention in a reaction medium. The terms "side product" or "byproduct" refer generally to a product derived from any component(s) of the reaction medium which is not the target product and is preferably separated therefrom.

As used herein, the ternms "fluorous tagging" or "fluorous tagged" refer generally to attaching a fluorous moiety or group (referred to as a "fluorous tagging moiety," "fluorous tagging group" or simply "fluorous tag") to a compound to create a "fluorous tagged compound". Preferably, the fluorous tagging moiety is attached via covalent bond. However, other strong attachments such as ionic bonding or chelation can also be used. In the present invention, fluorous tagging moieties are preferably used on different compounds to facilitate separation of fluorous tagged compounds from, for example, untagged organic compounds.

As used herein, the term "fluorous", when used in connection with an organic (carbon-containing) molecule, moiety or group, refers generally to an organic molecule, moiety or group having a domain or a portion thereof rich in carbon-fluorine bonds (for example, fluorocarbons, fluorohydrocarbons, fluorinated ethers and fluorinated amines). The terms "fluorous tagged reagent" or "fluorous reagent," thus refer generally to a reagent comprising a portion rich in carbon-fluorine bonds. As used herein, the term "perfluorocarbons" refers generally to organic compounds in which all hydrogen atoms bonded to carbon atoms have been replaced by fluorine atoms. The terms "fluorohydrocarbons" and "hydrofluorocarbons" include organic compounds in which at least one hydrogen atom bonded to a carbon atom has been replaced by a fluorine atom. The attachment of fluorous moieties to organic compounds is discussed for example, in U.S. Pat. Nos. 5;859,247, 5,777, 121 and U.S. patent application Ser. No. 09/506,779, and U.S. Provisional Patent Application Serial No. 60/281,646, assigned to the assignee of the present invention, the disclosures of which are incorporated herein by reference.

The terms "alkyl", "aryl" and other groups set forth herein refer generally to both unsubstituted and substituted groups unless specified to the contrary. Unless otherwise specified, alkyl groups are hydrocarbon groups and are preferably $C_1-C_{15}$ (that is, having 1 to 15 carbon atoms) alkyl groups, and more preferably $C_1-C_{10}$ alkyl groups, and can be branched or unbranched, acyclic or cyclic. The above definition of an alkyl group and other definitions apply also when the group is a substituent on another group (for example, an alkyl group as a substituent of an alkylamino group or a dialkylamino group). The term "aryl" refers to phenyl or naphthyl, and preferably phenyl. The term "alkoxy" refers to $-OR^a$, wherein $R^a$ is an alkyl group.

Separation of the compounds in the present invention is preferably achieved by using separation techniques that are complementary to (based upon differences between) the fluorous content. Compounds differing in fluorous content can be separated using a fluorous separation technique (for example, fluorous reverse phase chromatography). As used herein, the term "fluorous separation technique" refers generally to a method that is used to separate mixtures containing fluorous tagged molecules (or fluorous molecules) and organic (non-fluorous) molecules based predominantly on the difference in fluorous nature of molecules. Fluorous separation techniques include but are not limited to chromatography over solid fluorous phases such as fluorocarbon bonded phases or fluorinated polymers. See, for example, Danielson, N. D. et al., "Fluoropolymers and Fluorocarbon Bonded Phases as Column Packings for Liquid Chromatography," *J. Chromat.*, 544, 187–199 (1991); Kainz, S., Luo, Z. Y., Curran, D. P., Leitner, W., "Synthesis of Perfluoroalkyl-Substituted Aryl Bromides and Their Purification Over Fluorous Reverse Phase Silica", *Synthesis*, 1425–1427 (1998); and Curran, D. P., Hadida, S., He, M., "Thermal Allylations of Aldehydes with a Fluorous Allylstannane. Separation of Organic and Fluorous Products by Solid Phase Extraction with Fluorous Reverse Phase Silica Gel", *J. Org. Chem.*, 62, 6714–6715 (1997). Examples of suitable fluorocarbon bonded phases include commercial Fluofix® and Fluophase™ columns available from Keystone Scientific, Inc. (Bellefonte, Pa.), and FluoroSep™-RP-Octyl from ES Industries (Berlin, N.J.). Other fluorous separation techniques include liquid-liquid based separation methods such as standard separatory-funnel type extractions and countercurrent distribution with a fluorous solvent and an organic solvent.

The process of separation of the fluorous tagged reagents and byproducts of the present invention from the organic target product and other organic species takes only a few minutes and can be readily conducted in parallel, so it is highly suitable not only for individual reactions but also for combinatorial chemistry experiments with parallel reactions. The fluorous Mitsunobu reaction of the present invention is also economical since the mixture of fluorous byproducts can be readily separated and each of the products can be reconverted to the corresponding original fluorous reagents by standard chemical reactions.

In common organic synthesis, individual steps are conducted sequentially until the final target molecule or product is made. In combinatorial organic synthesis, the target is not a single molecule but instead a "library" of molecules. Combinatorial synthesis can be carried out by parallel synthesis of individual pure compounds or synthesis of mixtures.

In mixture and combinatorial synthesis, multiple reactions are conducted either together or in parallel to provide multiple products. In mixture synthesis and combinatorial synthesis, the premium of simple methods of purification is even higher than in normal synthesis. For this reason, combinatorial synthesis is now commonly conducted on the solid phase, where purification can be effected simply by filtration. However, conducting such reactions can be difficult because the solid-bound reaction component never truly dissolves in the reaction solvent.

BRIEF DESCRIPTION OF THE DRAWINGS

FIG. 1 illustrates a standard Mitsunobu reaction.

DETAILED DESCRIPTION OF THE INVENTION

Compounds bearing fluorous (fluorocarbon) tags can readily be separated from organic compounds lacking fluorous tags by fluorous separation techniques such as liquid-liquid extraction or solid-liquid extractions. By using appropriate fluorous reagents coupled with fluorous separation techniques, the products of the Mitsunobu reaction are readily separated from all reagent byproducts and unreacted reagents. The separation requires no additional chemical reactions and imposes no additional limitations on the Mitsunobu reaction. Moreover, the reagent byproducts can be recycled back to the original reagents.

Figure 2A:
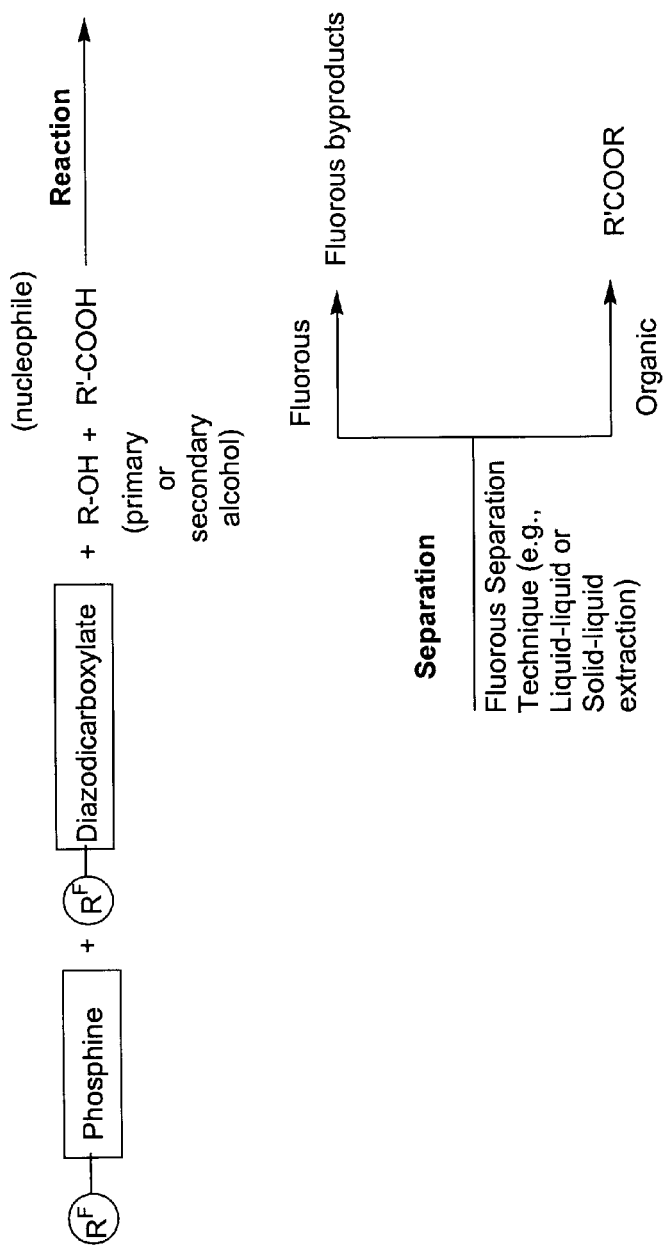
FIG. 2 illustrates an embodiment of a fluorous Mitsunobu reaction of the present invention.
Figure 2B:
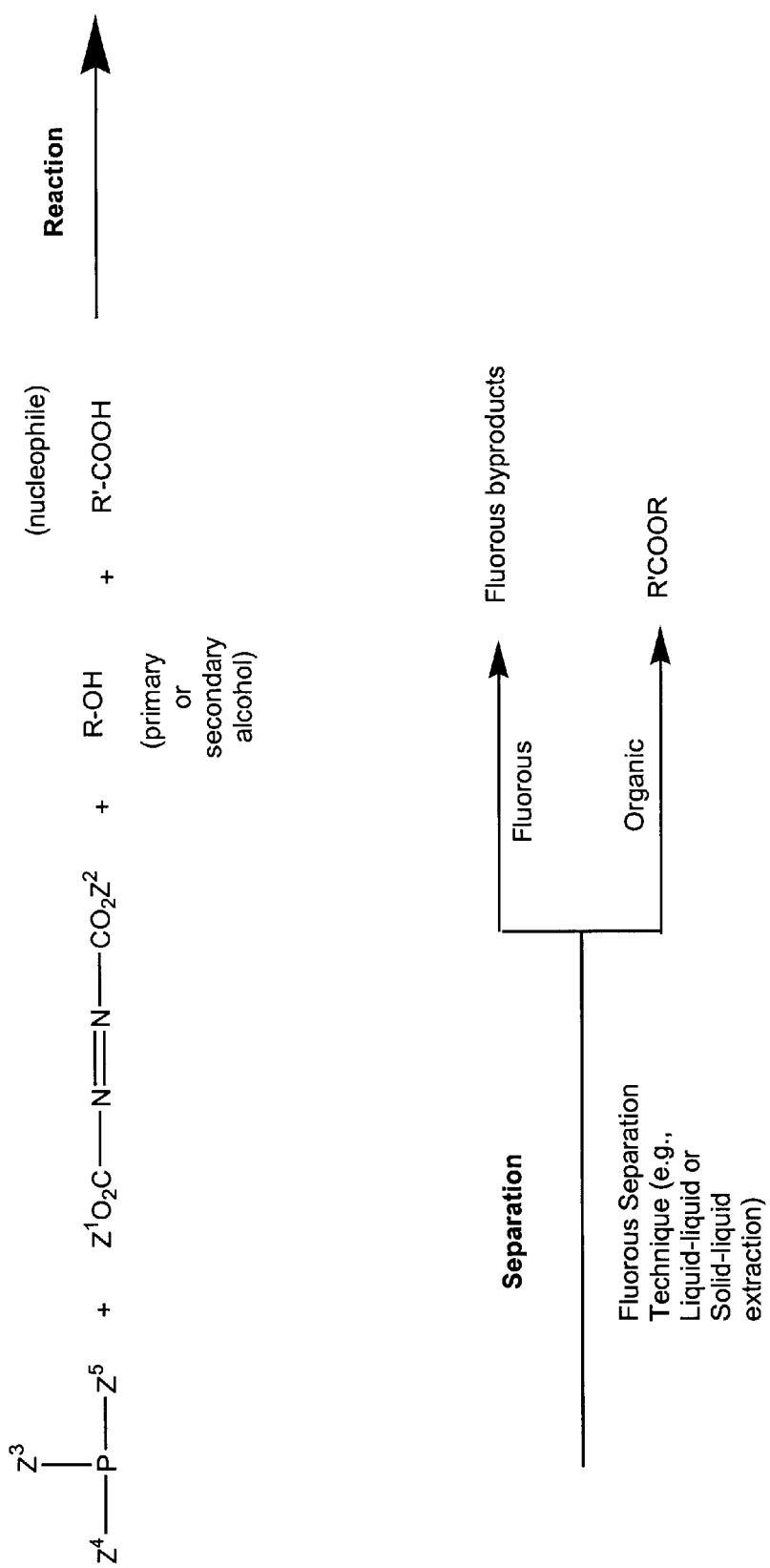

Phosphines with perfluoroalkyl chains have been used in the fluorous biphasic catalysis. However, fluorous phosphines have found only very limited use as stoichiometric reagents in reactions. In the present invention, Mitsunobu reactions employing a fluorous phosphine and a fluorous diazodicarboxylate allow isolation of the organic Mitsunobu adduct from the fluorous byproducts by a fluorous separation technique such as liquid-liquid extraction or solid-liquid extraction as illustrated generally in FIG. 2A. FIG. 2B illustrates Mitsunobu reactions employing representative fluorous phosphines and a fluorous diazodicarboxylates of the present invention in which $Z^1$, $Z^2$, $Z^3$, $Z^4$ and $Z^5$ are as described above.

Figure 3:
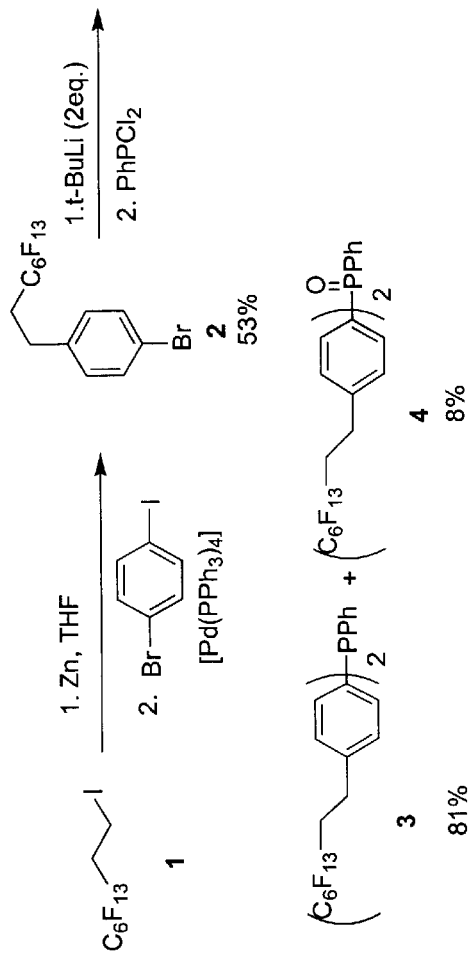
FIG. 3 illustrates the synthesis of fluorous phosphines.
Figure 4:
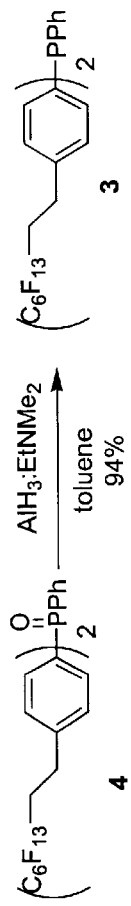
FIG. 4 illustrates the reduction of a fluorous phosphine oxide.

In several representative studies, a family of fluorous phosphines carrying different numbers of perfluoroalkyl chains was synthesized as illustrated in FIG. 3. Synthesis of fluorous phosphines is also discussed in U.S. Provisional Patent Application Serial No. 60/281,646. For example, 1-bromo-4-iodobenzene was coupled with the organozinc derived from perfluorohexylethyliodide 1. The bromobenzene 2 with the fluorous tag was then subjected to halogen-metal exchange, and the resulting aryllithium reagent was treated with dichlorophenylphosphine to form the fluorous phosphine 3 and the fluorous phosphine oxide 4, both containing two fluorous chains. The crude reaction mixture was then subjected to silica gel chromatography with gradient elution. The less polar fluorous phosphine 3 was eluted with 20:1 hexane:ethyl acetate and the more polar fluorous phosphine oxide 4 was eluted with 1:1 hexane:ethyl acetate. Fluorous phosphine was isolated as a colorless viscous oil (solidifies on standing for two weeks) in 81% yield and the fluorous phosphine oxide 4 was isolated as a colorless viscous oil in 8% yield. The fluorous phosphine oxide 4 isolated as the major byproduct from this reaction was easily reduced using, for example, alane as illustrated in FIG. 4. The fluorous phopshine 3 was isolated in 94% yield after silica gel chromatography (20:1 hexane:ethyl acetate) in the reduction of FIG. 4.

The fluorous phosphines were analyzed by fluorous reverse phase HPLC. The retention time of the fluorous phosphine 3 with two fluorous chains and the corresponding phosphine oxide 4, were found to be 29.8 min. and 28.3 min. with a gradient elution starting from 80% MeOH, 20% water (at t=0 min) to 100% MeOH (at t=30 min) to 90% MeOH, 10% THF (at t=60 min.). Triarylphosphines having one and three fluorous chains (structures not shown) had a retention time of 13.9 min. and 38.9 min. respectively; the retention times of the corresponding phosphine oxides (structures not shown) had a retention time of 10.6 min. and 37.7 min. respectively. In general, fluorous compounds preferably had a retention time of more than approximately 10 min. on the fluofix column (a fluorous reverse phase HPLC column) under the conditions of the experiments to facilitate separation thereof from organic compounds via fluorous solid phase extraction (FSPE). More preferably, the retention time of the fluorous compounds was more than approximately 14 min. On this basis, fluorous phosphine 3, having two fluorous chains was chosen for further studies of fluorous Mitsunobu reaction. The Pt complex prepared from the fluorous phosphine 3 was used as a catalyst in allylation of aldehydes and was found to be successful both at reaction stage and at separation stage. Although fluorous phosphine 3 was chosen for study, fluorous phosphines having only one fluorous chain are also suitable for use in the present invention using, for example, separation columns having higher resolution than the columns used in the present studies (as determined at least in part by the ability of the fluorous bonded phase of the column to retain fluorous molecules).

Figure 5:
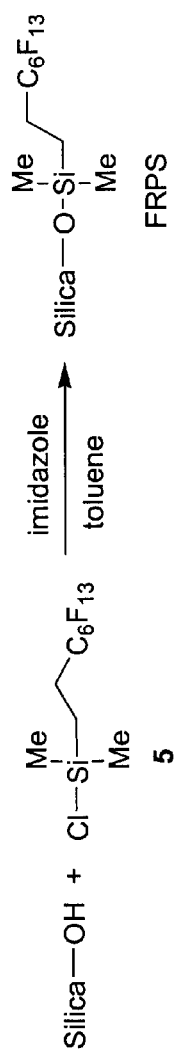
FIG. 5 illustrates synthesis of fluorous reverse phase silica gel.

Fluorous Reverse Phase Silica gel (FRPS) for use in FSPE was synthesized from normal silica gel by treatment with the commercially available fluorous silyl chloride 5 and imidazole in tolueneat 100° C. for 2 days as illustrated in FIG. 5. The FRPS obtained from this reaction was repeatedly washed with MeOH, water, THF and ether to remove any adsorbed impurities. Washing was continued until the washings were free from impurities as analyzed by $^1$H NMR. The resulting FRPS was dried overnight under high vacuum.

Figure 6:
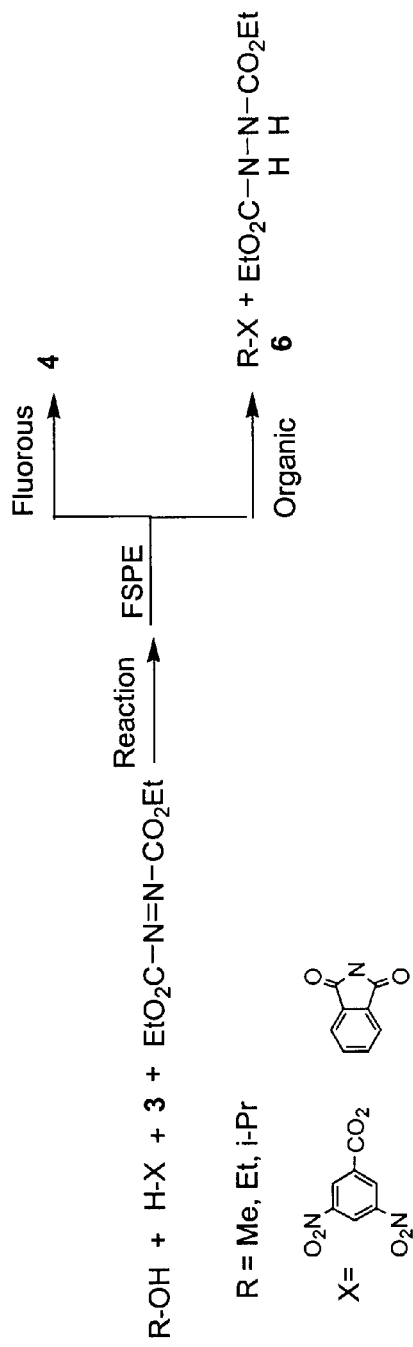
FIG. 6 illustrates esterification of 3,5-dinitrobenzoic acid and N-alkylation of phthalimide with methanol, ethanol and isopropanol using fluorous phosphine reagent and organic DEAD reagent.

The fluorous phosphine 3 was tested for its applicability in Mitsunobu reactions using classical, organic DEAD reagent. Esterification of 3,5-dinitrobenzoic acid and N-alkylation of phthalimide with methanol, ethanol and isopropanol were studied as illustrated in FIG. 6. Reactions with 3,5-dinitrobenzoic acid were conducted by adding a solution of 3 (1 equiv) and the alcohol (2 equiv) in ether to a solution of DEAD (1 equiv) and 3,5-dinitrobenzoic acid (1 equiv) in ether and stirring overnight. Reactions with phthalimide were done by adding a solution of DEAD (1 equiv) in THF to a solution of phthalimide (1 equiv), 3 (1 equiv), and the alcohol (2 equiv) and stirring overnight. At the end of the Mitsunobu reaction, the solvent was evaporated and the crude reaction mixture mixture (~200 mg) was taken up in methanol and was loaded on to 2 g of FRPS. Elution with 10 mL of 80% MeOH gave a mixture of the Mitsunobu adduct 6 and diethyl hydrazine dicarboxylate. The fluorous solid phase extraction completely removed the fluorous phosphine oxide. However, chromatography was needed to remove the hydrazine derivative. The isolated yields of 6 after normal silica gel chromatography are shown in Table 1.

TABLE 1

Yields For Mitsunobu Reaction With Fluorous Phosphine

| Entry | Alcohol | Product Structure | Yield |
|---|---|---|---|
| | | 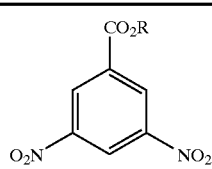 | |
| 1 | MeOH | R = Me | 87% |
| 2 | EtOH | R = Et | 76% |

TABLE 1-continued

Yields For Mitsunobu Reaction With Fluorous Phosphine

| Entry | Alcohol | Product Structure | Yield |
|---|---|---|---|
| 3 | i-PrOH | R = i-Pr | 76% |
| | | 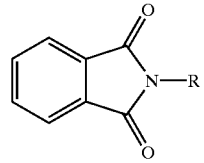 | |
| 4 | MeOH | R = Me | 91% |
| 5 | EtOH | R = Et | 78% |
| 6 | i-PrOH | R = i-Pr | 75% |

Figure 7:
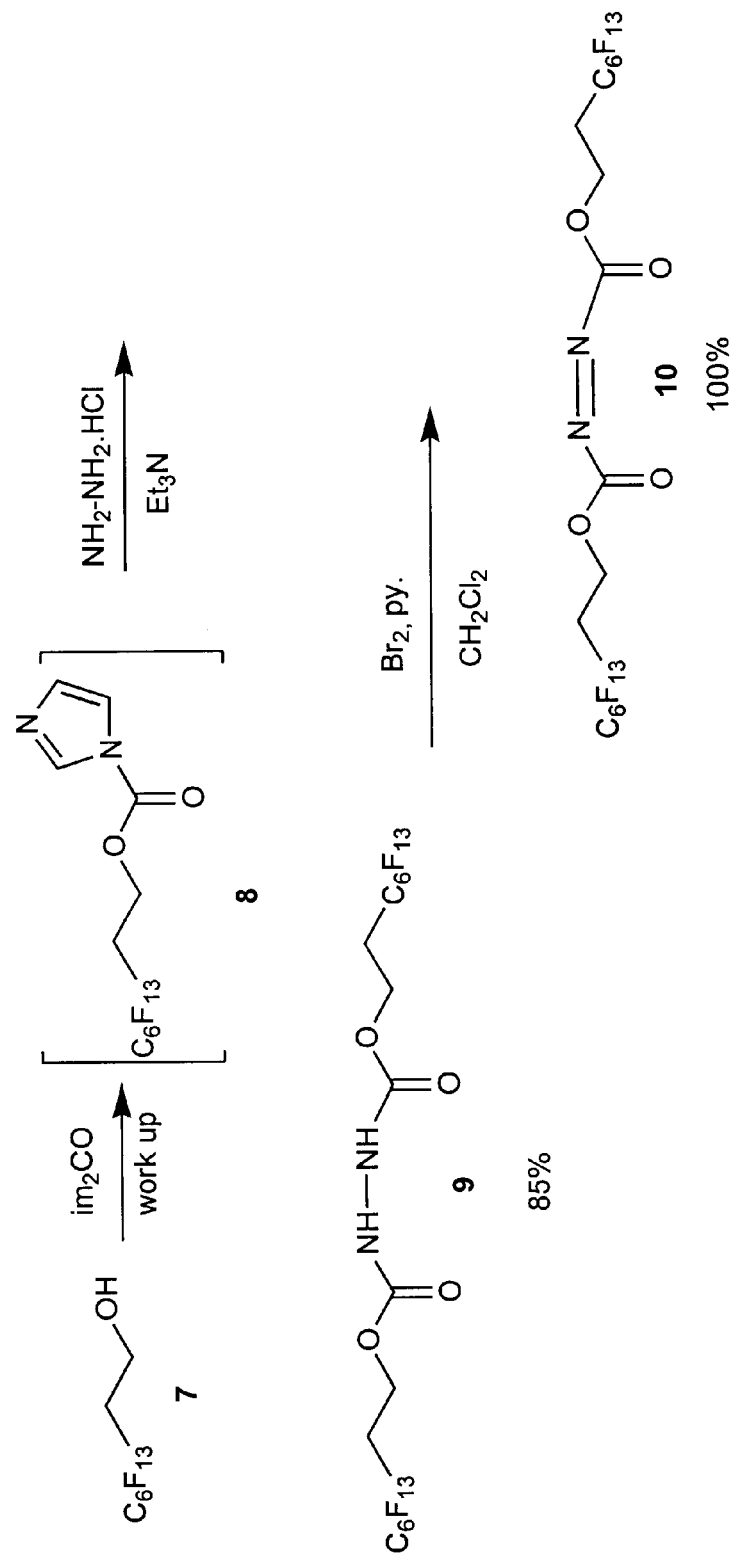
FIG. 7 illustrates synthesis of a fluorous DEAD reagent.

A fluorous DEAD reagent is preferably used to complement the fluorous phosphine to completely eliminate the need for chromatography. Therefore, a novel fluorus DEAD regent 10 carrying two perfluorohexylethyl chains was synthesized as shown in FIG. 7. 2-Perfluorohexyl ethanol 7 was treated with 1,1'-carbonyldiimidazole (1.2 equiv) at room temperature in THF to generate the imidazolide 8. Excess 1,1'-carbonyldiimidazole was quenched with water and the imidazolide from 8 (along with some imidazole) was extracted into ether. Without characterization the crude imidazolide 8 was then coupled with hydrazine generated in situ from hydrazine hydrochloride and triethylamine. The fluorous hydrazine 9 was isolated as a white powder in 85% yield after standard chromatography. Oxidation of 9 with iodobenzene diacetate gave relatively low yields and required chromatographic separation. However, oxidation of 9 proceeded smoothly in dichloromethane using bromine and pyridine. After stirring at room temeperature for 2 h, the reaction mixture was diluted with dichloromethane and washed with aqueous sodium sulfite, brine and water. The methylene chloride layer was dried and concentrated to give the fluorous DEAD reagent 10 as a yellow solid in quantitative yield. The purity of 10 obtained directly from this reaction after liquid-liquid extraction was excellent as judged by $^1$H, $^{13}$C and $^{19}$F NMR spectra and hence it was directly used without any further purification in all of the Mitsunobu type reactions described below. Comparable results were obtained by oxidation with the N-bromosuccinimide (NBS).

Figure 8:
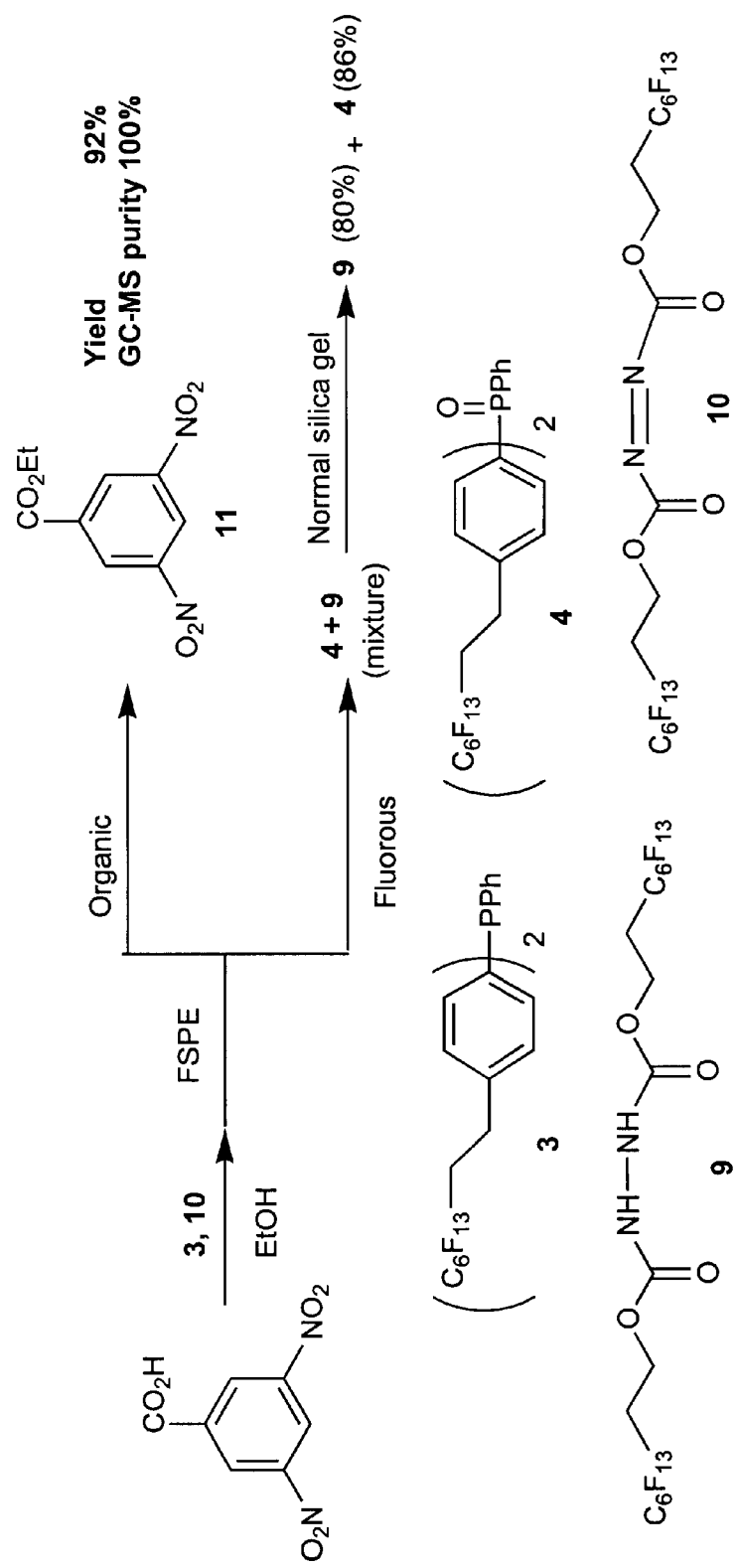
FIG. 8 illustrates a study of the reactivity of the fluorous DEAD reagent of FIG. 7.

To illustrate the reactivity of the fluorous DEAD reagent 10 in Mitsunobu reactions and the separation of the fluorous byproducts 9 and 4, 3,5-dinitrobenzoic acid was reacted with ethanol using 3 and 10 as illustrated in FIG. 8 using the same procedure described before. At the end of the reaction, the solvent was evaporated, the crude reaction mixture (~200 mg) was taken up in MeOH and loaded on to 2 g of FRPS. Elution with 80% MeOH gave the Mitsunobu adduct 11 in 92% yield free of any impurities as judged from GC-MS analysis and $^1$H NMR spectrum. Elution with ether gave a mixture of the fluorous phosphine oxide 4 and the fluorous hydrazine 9. This fluorous byproduct mixture was separated on normal silica gel with 3:2 hexane:EtOAc as the solvent system. The less polar fluorous hydrazine 9 eluted first and was isolated in 80% yield; the more polar fluorousphosphine oxide 4 was isolated in 86% yield.

The ease of separation of the fluorous reagent based byproducts 4 and 9 is useful because the reagents can then be recycled. Both the reduction of the fluorous phosphine oxide 4 and the oxidation of the fluorous hydrazine 9 are very clean reactions and in each case the product can be isolated in almost quantitative yields.

Figure 9:
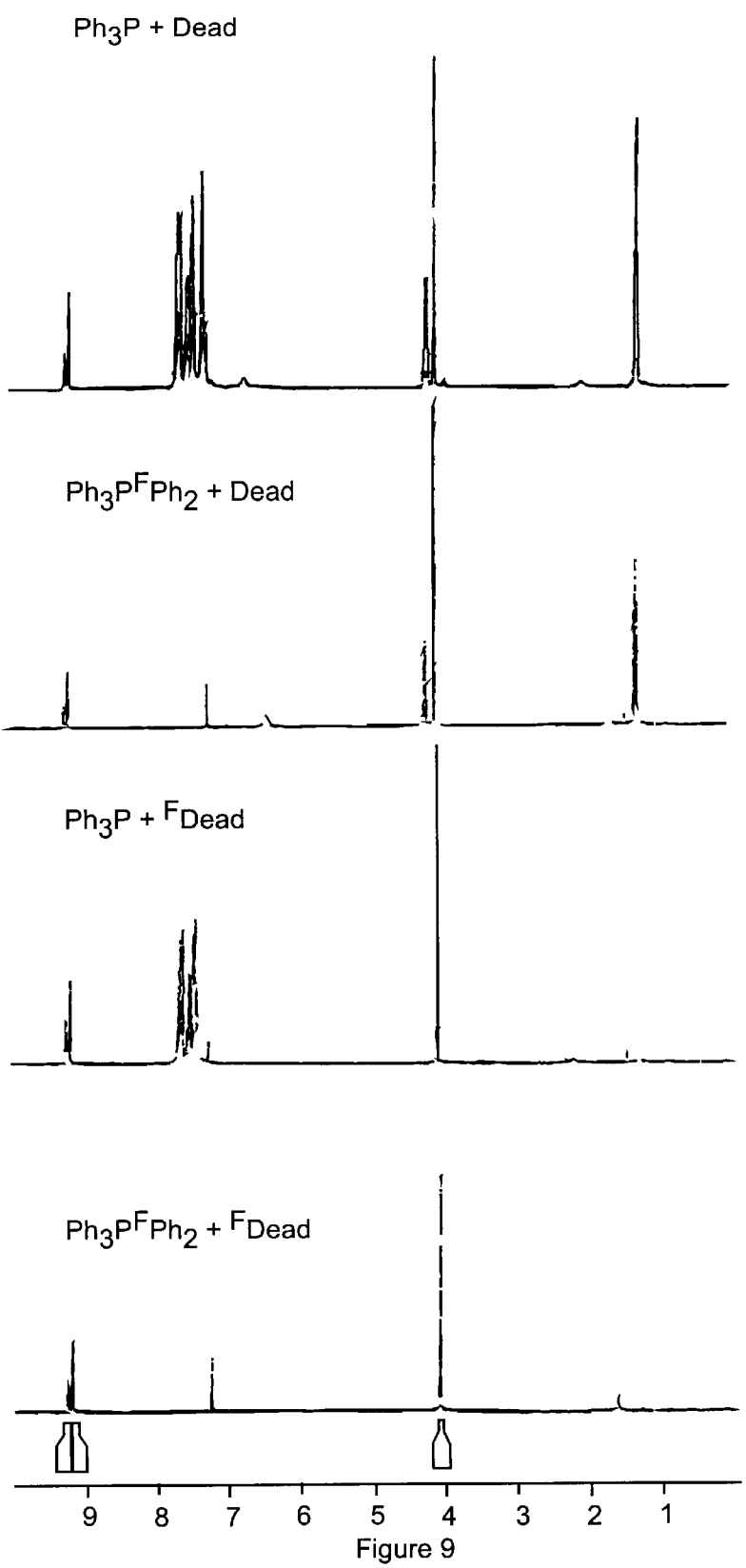
FIG. 9 illustrates NMR spectra of several experiments with fluorous and non-fluorous (standard) Mitsunobu reagents.

Several experiments were also carried out to demonstrate the compatibility of the fluorous Mitsunobu reagents 3 and 10 with each other and with the regular organic reagents triphenylphosphine and DEAD. 3,5-Dinitrobenzoic acid was reacted with MeOH with all possible combinations of fluorous and organic reagents using the procedure described above. After stirring overnight, solvent was evaporated and each reaction mixture was individually subjected to FSPE. The organic fraction from each experiment was concentrated and analyzed by $^1$H NMR spectroscopy. The results of these experiments are summarized in Table 2. In Table 2 and elsewhere herein, $^F$Ph refers to a fluorous phenyl group and $^F$DEAD refers to the fluorous DEAD reagent. Only in the case where both fluorous reagents were used, was the pure product isolated. In all the other cases, a mixture of product and organic reagent based byproduct(s) was isolated. The results indicate that fluorous chains are necessary to achieve separation in fluorous silica gel. The NMR spectra from all of the four experiments are illustrated in FIG. 9.

TABLE 2

Compatibility Of Organic And Fluorous Mitsunobu Reagents

| Entry | Reagents used | Organic fraction from FSPE* |
|---|---|---|
| 1 | PhP$^F$Ph$_2$ + $^F$DEAD | 12 |
| 2 | Ph$_3$P + $^F$DEAD | 12 + 13 |
| 3 | PhP$^F$Ph$_2$ + DEAD | 12 + 14 |
| 4 | Ph$_3$P + DEAD | 12 + 13 + 14 |

*Analyzed by $^1$H NMR spectroscopy
13 = Triphenyl phosphine oxide   14 = Diethyl hydrazine dicarboxylate
12 = Methyl 3,5-dinitrobenzoate Several parallel experiments were conducted to illustrate the scope of the fluorous reagents with other Mitsunobu substrates. Experiments with 3,5-dinitrobenzoic acid and phthalimide with three different alcohols (MeOH, allyl alcohol and p-fluorobenzylalcohol) were conducted with the procedure described before. Results are summarized in Table 3. The Mitsunobu product from p-fluorbenzyl alcohol has one fluorine atom, and shows a single peak in $^{19}$F NMR spectrum which can be used for estimating fluorous contamination in the product. Both N-p-fluorobenzyl phthalimide and p-fluorobenzyl 3,5-dinitrobenzoate showed only one peak in their $^{19}$F NMR spectra indicating the absence of any fluorous impurities in the product. The yield of the product was determined from the mass of the residue from organic fraction after FSPE and purity was determined from integration of peaks in the gas chromatogram.

TABLE 3

Fluorous Mitsunobu Reactions With 3,5-Dinitrobenzoic Acid And Phthalimide

| Entry | Alcohol | Product Structure | Yield | GC-MS Purity |
|---|---|---|---|---|
| 1 | CH$_3$OH | R = CH$_3$ | 93% | 100% |
| 2 | allyl-OH | R = allyl | 85% | 100% |
| 3 | F-C$_6$H$_4$-CH$_2$OH | R = F-C$_6$H$_4$-CH$_2$- | 75% | 91% |
| 4 | CH$_3$OH | R = CH$_3$ (phthalimide) | 91% | 100% |

TABLE 3-continued

Fluorous Mitsunobu Reactions With 3,5-Dinitrobenzoic Acid And Phthalimide

| Entry | Alcohol | Product Structure | Yield | GC-MS Purity |
|---|---|---|---|---|
| 5 | (allyl alcohol) | R = (allyl) | 79% | 100% |
| 6 | 4-fluorobenzyl alcohol | R = 4-fluorobenzyl | 75% | 100% |

N-(t-Butoxycarbonyl)-p-toluene sulfonamide is another interesting substrate for Mitsunobu reactions. The product of that reaction can be converted to boc-protected amines on treatment with sodium naphthalenide. N-(t-Butoxycarbonyl)-p-toulene sulfonamide was subjected to Mitsunobu reaction in THF with methanol using fluorous regents 3 and 10 under standard conditions (addition of a solution of $^F$DEAD (1.5 equiv) in THF to a solution of N-(t-butoxycarbonyl)-p-toluene sulfonamide (1 equiv), 3 (1.5 equiv), and the alcohol (1.5 equiv) in THF). After 3 h at room temperature, TLC analysis (10:3 hexane:EtOAc) showed complete conversion of the starting material. The solvent was then evaporated and the crude reaction mixture was subjected to FSPE. N-(t-Butoxycarbonyl)-p-toluene sulfonamide was isolated in 100% yield from the organic fraction of FSPE. $^1$H NMR analysis also confirmed complete conversion of the starting material. However, when alkylation of-N-(t-butoxycarbonyl)-p-toluene sulfonamide was attempted with allyl alcohol and p-fluorobenzyl alcohol with the standard procedure used for methanol, TLC showed the presence of starting material even after stirring overnight. Each reaction mixture was then individually subjected to FSPE, and the residue from organic fraction was analyzed by $^1$H NMR spectroscopy. Not surprisingly, both of the $^1$H NMR spectra showed the presence of starting material. Addition of molecular sieves to the reaction, did not improve conversion. The results of these "normal mode of addition" studies with N-(t-butoxycarbonyl)-p-toluene sulfonamide are summarized in Table 4.

TABLE 4

Fluorous Mitsunobu Reactions With N-(t-Butoxycarbonyl)-p-toluene Sulfonamide Under Standard Conditions

| Alcohol | Conditions | Conversion* |
|---|---|---|
| MeOH | THF, RT | 100% |
| allyl alcohol | THF, RT | 41% |
| p-fluorobenzyl alcohol | THF, RT | Trace |

TABLE 4-continued

Fluorous Mitsunobu Reactions With N-(t-Butoxycarbonyl)-p-toluene Sulfonamide Under Standard Conditions

| Alcohol | Conditions | Conversion* |
|---|---|---|
| p-fluorobenzyl alcohol | THF + mol. Sieves, RT | Trace |

*determined by $^1$H NMR

The order of addition of reagents, in some cases, can have a substantial effect on the Mitsunobu reaction. Therefore a different mode of addition than described above was studied. In that regard, a solution of fluorous DEAD reagent 10 (1.5 equiv) in THF was added to a solution of fluorous phosphine 3 (1.5 equiv) in THF at 0° C., then allyl alcohol (1.5 equiv) was added neat and finally the N-(t-butoxycarbonyl)-p-toluene sulfonamide (1 equiv). After 3 h, TLC (10:3 hexane:EtOAc) showed complete conversion of starting material. The solvent was then evaporated and the reaction mixture was subjected to FSPE. The organic fraction from FSPE was then concentrated. $^1$H NMR analysis of the residue from organic fraction revealed 91% conversion to N-allyl-N-(t-butoxycarbonyl)-p-toluene sulfonamide. In a similar way, the reaction with methanol and p-fluorobenzyl alcohol also gave very good conversions. The results from this mode of addition are summarized in Table 5. Once again, N-p-fluorobenzyl-N-(t-butoxycarbonyl)-p-toluene sulfonamide showed a single peak in $^{19}$F NMR spectrum indicating absence of fluorous impurities in the product. Yields were determined from the mass of the residue from organic fraction after FSPE; conversions were determined from $^1$H NMR analysis of the organic fraction and purities were determined from integration of peaks of gas chromatogram of each sample.

TABLE 5

Fluorous Mitsunobu Reactions With N-(t-butoxycarbonyl)-p-toluene sulfonamide Under Reverse Mode Of Addition Product Structure: aryl-SO$_2$NCO$_2^t$Bu with R substituent on N

| Entry | Alcohol | Product R group | Conversion | Yield | GC-MS Purity |
|---|---|---|---|---|---|
| 1 | CH$_3$OH | R = CH$_3$ | 100% | 90% | 100% |
| 2 | allyl-OH | R = allyl | 91% | 95% | 100% |
| 3 | 4-F-C$_6$H$_4$-CH$_2$OH | R = 4-F-C$_6$H$_4$-CH$_2$- | 96% | 88% | 100% |

To test the generality of the above "reverse" mode of addition, three fluorous Mitsunobu reactions were carried out with 4-(4-nitrophenyl)butyric acid and three different alcohols (methanol, allyl alcohol and p-fluorobenzyl alcohol). The fluorous phosphine 3 (1.5 equiv) and the fluoruos DEAD 10 (1.5 equiv) were mixed in THF at 0° C. to generate the adduct, then alcohol (1.5 equiv) was added followed by 4-(4-nitrophenyl)butyric acid (1 equiv). After stirring overnight, the reaction mixture was subjected to FSPE and the organic fraction was analyzed by $^1$H NMR and GC-MS studies. The results are summarized in Table 6. Conversions were determined from $^1$H NMR analysis; yields were calculated from the mass of organic fraction from FSPE and the purities were determined from integration of peaks in gas chromatogram.

presence of bis(triphenylphosphine) platinum dichloride showed differences. Reaction with the fluorous allyl tin 16 with three methylene (propylene) spacers were faster and gave cleaner products compared to the fluorous allyl tin 15 with two methylene (ethylene) spacers.

Figure 11:
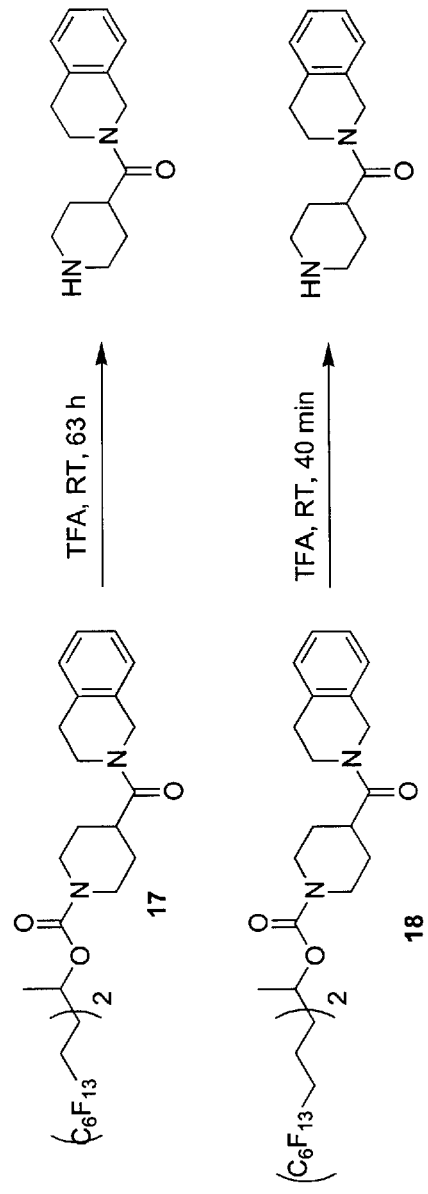
FIG. 11 illustrates the effect of the number of methylene groups in a spacer group for fluorous boc protected amines.

Similarly, the fluorous boc protected amines 17 and 18 showed differences in reactivity (see FIG. 11). The fluorous boc protected amide 17 having two methylene spacers underwent deprotection slowly (63 h), while 18 carrying three methylene spacers was deprotected in 40 min, under the same conditions. Therefore, the effect of the length of the spacer in fluorous diazodicarboxylates was studied.

Figure 12:
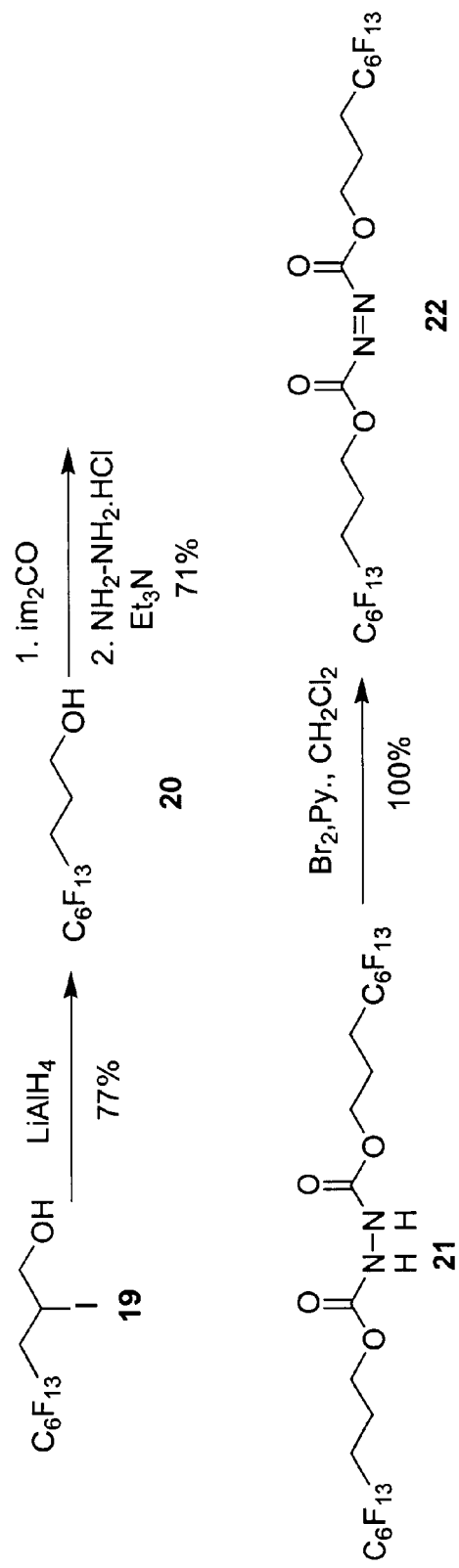
FIG. 12 illustrates the synthesis of fluorous diazodicarboxylate having three methylene spacers.

In that regard, fluorous diazodicarboxylate 22 having three methylene spacers was synthesized as shown in FIG. 12. The iodoalcohol 9 was reduced with LiAlH$_4$ and the

TABLE 6

Fluorous Mitsunobu Reactions with 4-(4-Nitrophenyl)butyric acid with Reverse Mode of Addition Product Structure: O$_2$N-C$_6$H$_4$-(CH$_2$)$_3$-CO$_2$R

| Entry | Alcohol | Product R group | Conversion | Yield | GC-MS Purity |
|---|---|---|---|---|---|
| 1 | CH$_3$OH | R = CH$_3$ | 100% | 93% | 100% |
| 2 | allyl-OH | R = allyl | 100% | 78% | 100% |
| 3 | 4-F-C$_6$H$_4$-CH$_2$OH | R = 4-F-C$_6$H$_4$-CH$_2$- | 100% | 88% | 100% |

Figure 10:
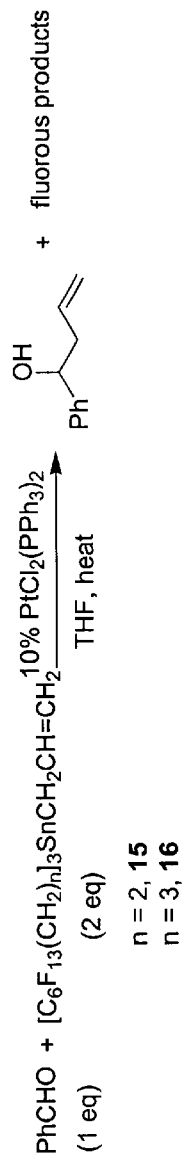
FIG. 10 illustrates the effect of the number of methylene groups in a spacer group for fluorous allyl tins.

The number of intervening methylene groups in the spacer of a fluorous reagent can alter its reactivity in certain, but not all, cases. For example, the allylation of benzaldehyde with fluorous allyl tins 15 and 16 (see FIG. 10) in the alcohol 20 with the propylene spacer was isolated in 77% yield after distillation. The alcohol 20 was then reacted with 1,1'-carbonyldiimidazole and the crude imidazolide was coupled with hydrazine to give 21 which was isolated in 71% yield as a white solid after chromatography. Once again, oxidation of the fluorous hydrazine 21 proceeded well to give 22 as an yellow solid in quantitative crude yield.

The crude fluorous DEAD reagent 22 was then used in Mitsunobu reactions with N-Boc-p-toluenesulfonamide. Once again, the standard mode of addition gave complete conversion with MeOH and the product, N-methyl-N-boc-p-toluenesulfonamide was isolated in 85% yield after FSPE. However, the allyl alcohol gave only trace conversion of the starting material. The organic fraction after FSPE was mostly starting material. These results are summarized in Table 7.

TABLE 7

Fluorous Mitsunobu Reactions (Using $^F$DEAD With Propylene Spacers) With N-(t-butoxycarbonyl)-p-toluene sulfonamide Under Standard Mode Of Addition

| Alcohol | Conditions | Conversion* |
| --- | --- | --- |
| MeOH | THF, RT | 100% |
| 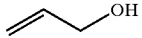 | THF, RT | Trace |

*determined by $^1$H NMR spectroscopy

EXAMPLES

Unless otherwise noted, all reagents were used directly from a commercial source without any further purification. Diethyl ether, THF and toluene were distilled from sodium/benzophenone under nitrogen; dichloromethane was distilled from calcium hydride. NMR spectra were recorded at 300 MHz for $^1$H, 75 MHz for $^{13}$C, 285 MHz for $^{19}$F and 121.5 MHz for $^{31}$P. Unless otherwise specified, chemical shift values are in parts per million (ppm) using CHCl$_3$ as reference for $^1$H and $^{13}$C; 80% H$_3$PO$_4$ for $^{31}$P and CFCl$_3$ for $^{19}$F. Infrared spectra were obtained from an IBM IR/32 system and samples were run as thin films. Low resolution mass spectra (LRMS) were recorded on a Hewlett Packard-9000 GC-MS system. High resolution mass spectra (HRMS) were recorded on a varian MATCH-5 DF spectrometer. Melting points were measured on a MEL-TEMP II apparatus and were not corrected.

Example 1

1-Bromo-4-(3,3,4,4,5,5,6,6,7,7,8,8-tridecafluorooctyl)benzene (2)

Zinc powder (8.23 g, 125.8 mmol) was placed in a 250 mL round bottom flask equipped with a dropping funnel and a condenser. Zn was dried under vacuum and cooled under Argon. Freshly distilled THF (17.5 mL) was added at room temperature and the mixture stirred for 5 min. 1,2-Dibromoethane (0.5 mL) was added at 65° C. and the reaction flask was maintained at this temperature for 2 min and then cooled to room temperature. Chlorotrimethylsilane (0.5 mL) was added at room temperature. After 20 min, a solution of 1,1,1,2,2,3,3,4,4,5,5,6,6,-tridecafluro-8-iodooctane (50 g, 105.5 mmol) in THF (88 mL) was added dropwise. The rate of addition was adjusted such that the reaction mixture was maintained at room temperature. After 24 h at room temperature, the colorless organozinc was cannulated to a 250 mL round bottom flask equipped with a condenser and charged with 1-bromo-4-iodobenzene (30.75 g, 108.7 mmol), tetrakis(triphenylphosphine) palladium(0) (4.3 g, 3.7 mmol) in THF (52.5 mL). The reaction mixture was stirred at 45° C. for 24 h. The solvent was then removed under reduced pressure; the crude residue was dissolved in methylene chloride (50 mL) and was extracted with FC-72 (7×50 mL). FC-72 layers were combined and the solvent was evaporated. The crude product obtained was then distilled under low pressure to give 2 (28 g, 53%) as a colorless oil: bp 81° C./0.03 mmHg; $^1$H NMR (CDCl$_3$) δ7.45 (d, J=8.4 Hz, 2H), δ7.11 (d, J=8.4 Hz, 2H), δ2.86–2.92 (m, 2H), δ2.36 (tt, J=18.3, 9.1 Hz, 2H)

Example 2

Phenyl-bis-[4-(3,3,4,4,5,5,6,6,7,7,8,8,8-tridecafluorooctyl)phenyl]phosphane (3)

A solution of t-BuLi (1.7 M in pentane, 3.4 mL, 2.9 mmol) was added slowly to 1-bromo-4-(3,3,4,4,5,5,6,6,7,7,8,8-tridecafluoro-octyl)benzene 2 (1.48 g) in ether (73 mL) at −78° C. After 1 h at −78° C., dichlorophenylphosphine (196 µl, 1.45 mmol) was added and the reaction mixture was warmed to room temperature and stirred overnight. Then the reaction mixture was quenched with water (10 mL). The ether layer was separated. The aqueous layer was further extracted with ether (3×10 mL). The ether layers were then combined, dried with magnesium sulfate and concentrated under reduced pressure. The residue was then purified by column chromatography on silica gel with gradient elution. Elution with 20:1 hexane:ethylacetate gave,3 (1.13 g, 81%) as colorless oil which solidifies (mp 35–37° C.) on standing for two weeks in the refrigerator. Further elution with 1:1 hexane:ethylacetate gave 4 (0.114 g, 8%) as a colorless oil.

(3)$^1$H NMR (CDCl$_3$) δ7.20–7.36 (m, 13H), δ2.91–2.97 (m, 4H), δ2.31–2.48 (m, 4H); $^{31}$P NMR (CDCl$_3$) δ–5.91. (4) $^1$H NMR (CDCl$_3$) δ7.67–7.31 (m, 13H), δ3.00–2.95 (m, 4H), δ2.47–2.32 (m, 4H); $^{13}$P NMR (CDCl$_3$) δ29.3

Example 3

Procedure for Reduction of fluorous phosphine oxide (4)

A solution of alane-N,N-dimethyethyllamine complex (0.5M in toluene, 6.24 mL, 3.12 mmol) was slowly added to a solution of 4 (2.02 g, 2.08 mmol) in toluene (20 mL). After stirring at 90° C. for 3 h, the reaction mixture was cooled to room temperature, quenched with methanol (3 mL) and passed through a short column of celite. The celite column was then washed with hot THF and the washings were added to the filtered reaction mixture, which was concentrated and subjected to silica gel chromatography (20:1 hexane:ethylacetate) to obtain 3 (1.87 g, 94%).

Mitsunobu reactions of 3,5-dinitrobenzoic acid promoted by fluorous phosphine 3 and DEAD were done by Procedure A (see below). The amount of reagents and substrate used are fluorous phosphine 3 (200 mg, 0.21 mmol), alcohol (0.42 mmol), DEAD (33 µl, 0.21 mmol) and 3,5-dinitrobenzoic acid (44 mg, 0.21 mmol).

Example 3.1

Methyl 3,5-dinitrobenzoate

CAS Registry Number [2702-58-1]; $^1$H NMR (CDCl$_3$) δ9.25 (t, J=2 Hz, 1H), δ9.19 (d, J=2 Hz, 2H), δ4.08 (s, 3H); LRMS m/z (relative intensity) 226 (M$^+$, 18%), 195 (100%), 149 (45%), 75 (82%).

Example 3.2

Ethyl 3,5-dinitrobenzoate

CAS Registry Number [618-71-3];$^1$H NMR (CDCl$_3$) δ9.23 (t, J=2.1 Hz, 1H), δ9.18 (d, J=2.1 Hz), δ4.53 (q, J=7.1 Hz, 2H) δ1.49 (t, J=7.1 Hz, 2H); LRMS (relative intensity) 240 (M$^+$, 19%), 195 (81%), 180 (47%), 149 (43%), 75 (100%).

Example 3.3

Isopropyl 3,5-dinitrobenoate

CAS Registry Number [10477-99-3]; $^1$H NMR (CDCl$_3$) δ9.23 (t, J=2 Hz, 1H), δ9.16 (d, J=2.1 Hz, 2H), δ5.43–5.31 (m, 1H), 1.46 (d, J=6.1 Hz); LRMS (relative intensity) 254 (M$^+$, 2%), 213 (33%), 195 (100%), 149 (40%), 75 (76%).

N-alkylation of phthalimide using fluorous phosphine 3 and DEAD were done by Procedure B (see below). Amount of reagents and substrates used are DEAD (33 μl, 0.210 mmol), phthalimide (30 mg, 0.210 mmol), alcohol (0.420 mmol) and fluorous phosphine 3 (200 mg, 0.420 mmol).

Example 3.4

N-Methyl phthalimide

CAS Registry Number [550-44-7]; $^1$H NMR CDCl$_3$) δ7.86–7.82 (m, 2H), 7.73–7.70 (m, 2H), 3.19 (s, 3H); LRMS m/z (relative intensity) 161 (M$^+$, 100%), 104 (33%), 76 (30%).

Example 3.5

N-Ethyl phthalimide

CAS Registry Number [5022-29-7]; $^1$H NMR (CDCl$_3$) δ7.86–7.82 (m, 2H), 7.73–7.69 (m, 2H), 3.75 (q, J=7.3 Hz, 2H) 128 (t,=7.2 Hz, 3H); LRMS m/z (relative intensity) 175 (M$^+$, 100%), 160 (100%), 105 (26%), 76 (28%).

Example 3.6

N-Isopropyl phthalimide

CAS Registry Number [304-17-6] $^1$H NMR (CDCl$_3$) δ7.74–7.71 (m, 2H), 7.62–7.59 (m, 2H), 4.44 (m, 1H), 1.40 (d, J=6.9 Hz, 6H); LRMS m/z (relative intensity) 189 (M$^+$, 47%), 174 (100%).

Example 4

Bis(3,3,4,4,5,5,6,6,7,7,8,8-tridecafluorooctyl) hydrazine dicarboxylate (9).

3,3,4,4,5,5,6,6,7,7,8,8-Tridecafluoro-1-octanol 7 (10 g, 27.5 mmol) was slowly added to a solution of 1,1'-carbonyldiimidazole (5.35 g, 33 mmol) in THF (80 mL). After stirring for 30 min at room temperature, the crude reaction mixture was taken up in ether (200 mL) and quenched with water (40 mL). The aqueous layer was further extracted with ether (3×20 mL). The organic layers were combined and dried with magnesium sulfate. The solvent was removed under reduced pressure and the residue was dried under high vacuum. The crude imidazolide 8 was taken up in THF (14 mL) and hydrazine monohydrocholoride (942 mg, 13.75 mmol) and triethylamine (9.6 mL, 68.75 mmol) were added at room temperature. After 3 d, the reaction mixture was quenched with water (50 mL) and extracted with ether (3×50 mL). The organic layers were combined, dried with magnesium sulfate and concentrated. Flash column chromatography on silica gel (3:2 hexane-:ethyl acetate) gave bis(3,3,4,4,5,5,6,6,7,7,8,8-tridecafluorooctyl)hydrazine dicarboxylate 9 (9.52 g, 85%) as a white solid: mp 105° C. $^1$H NMR (acetone-d$^6$) δ8.48 (b, 2H), δ4.32 (t, J=6.1 Hz, 4H), δ2.70 (m, 4H); $^3$C NMR (acetone-d$^6$) δ156.2, 121.4–108.3 (m), 57.2, 30.2 (t, J=84.9 Hz); $^{91}$F NMR δ–80.6 NMR 6 –80.6 (3F), –112.9 (2F), –121.4 (2F), –122.4 (2F), –123.0 (2F), –126.3 (2F); IR (thin film): 1743 cm$^{-1}$, 3271 cm$^{-1}$; HRMS: calculated (812.0225), found (812.0239)

Example 5a

Bis(3,3,4,4,5,5,6,6,7,7,8,8-tridecafluorooctyl)diazo dicarboxylate 10

The fluorous hydrazine 9 (2 g, 2.46 mmol) and pyridine (0.4 mL, 4.92 mmol) were taken up in methylene chloride (25 mL) and the mixture was cooled to 0° C. Bromine (590 mg, 3.69 mmol) was slowly added. The ice bath was removed after the addition and the reaction was vigorously stirred at room temperature for 2 h. The reaction mixture was then diluted with methylene chloride (150 mL) and was washed with sodium sulfite solution, sodium bicarbonate solution, brine and water. The organic layer was dried with magnesium sulfate and concentrated to give bis(3,3,4,4,5,5,6,6,7,7,8,8-tridecafluorooctyl)diazo dicarboxylate as a yellow solid (1.99 g, 100%). mp 61° C.: $^1$H NMR (acetone-d$^6$) δ4.87 (t, J=5.9 Hz, 4H), δ2.91 (tt, J=5.9, 19 Hz, 4H); $^{13}$C NMR (acetone-d$^6$) δ161.2, 125–104(m), 62.7, 31.3 (t, J=85.1 Hz); $^{19}$F NMR (acetone d$^6$) δ–80.6 (3F), –112.9 (3F), –121.3 (2F), –122.3 (2F), –123 (2F), –123.6 (2F), –125.7 (2F); IR (thinfilm): 1787 cm$^{-1}$;LRMS 812.(M$^+$+2, 55%), 449 (91%), 327(85%), 131 (100%).

Example 5b

Bis(3,3,4,4,5,5,6,6,7,7,8,8-tridecafluorooctyl)diazo dicarboxylate 10

N-Bromosuccinimide (200 mg, 0.295 mmol) was added to a solution of the fluorous hydrazine 9 (200 mg, 0.246 mmol) and pyridine (40 μL, 0.492 mmol) in THF (2 mL) cooled to 0° C. The ice bath was removed and stirring was continued at room temperature for 1 h. The reaction mixture was then quenched with water and extracted with ether. The ether layers were combined, washed with 5% HCl and water, dried with magnesium sulfate and concentrated to give bis(3,3,4,4,5,5,6,6,7,7,8,8-tridecafluorooctyl)diazo dicarboxylate 10 as a yellow solid (198 mg, 100%).

Example 6

Mitsunobu reactions of 3,5-dinitrobenzoic acid promoted by fluorous phosphine 3 and fluorous DEAD 10 (Procedure A)

A solution of fluorous phosphine 3 (100 mg, 0.105 mmol) and an alcohol (0.105 mmol) in THF (0.5 mL) was slowly added to a solution of fluorous DEAD 10 (85 mg, 0.105 mmol) and 3,5-dinitrobenzoic acid (15 mg, 0.07 mmol) in THF (0.5 mL). After stirring overnight, the solvent was evaporated from the reaction mixture and the residue was loaded on to 2 g of FRPS using methanol. Elution with 80% MeOH (10 mL) gave 3,5-dinitrobenzoyl ester. A second elution with ether was done to collect the mixture of fluorous phosphine oxide 4 and fluorous hydrazine 9.

Example 6.1

Allyl 3,5-dinitrobenzoate $^1$H NMR (CDCl$_3$) δ9.25 (t, J=2 Hz, 1H), δ9.19 (d, J=2 Hz, 2H), δ6.14–6.01 (m, 1H), δ5.49 (dd, J=17.2, 1.3 Hz, 1H), δ5.41 (dd, J=10.4, 1 Hz, 1H), δ4.96 (dt, J=6, 1 Hz); LRMS m/z (relative intensity) 195 (M$^+$, 100%), 149 (38%), 75 (56%).

Example 6.2 p-Fluorobenzyl 3,5-dinitrobenzoate $^1$H NMR δ9.24 (t, J=2.1 Hz, 1H), δ9.15 (d, J=2.1 Hz, 2H), δ7.51–7.45 (m, 2H), δ7.16–7.09 (m, 2H), 5.45 (s, 2H); $^{19}$F NMR (CDCl$_3$) −110.8; LRMS m/z (relative intensity) 320 (M$^+$, 8%), 196 (33%), 109 (100%).

Example 7

General procedure for Mitsunobu reactions of phthalimide promoted by fluorous phosphine 3 and fluorous DEAD 10 (Procedure B)

A mixture of fluorous DEAD 10 (85 mg, 0.105 mmol) in THF (0.5 mL) was slowly added to a solution of phthalimide (10 mg, 0.07 mmol), an alcohol (0.105 mmol) and fluorous phosphine 3 (100 mg, 0.210 mmol) in THF (0.5 mL). After stirring overnight, the solvent was evaporated from the reaction mixture and the residue was loaded on to 2 g of FRPS using methanol. Elution with 80% MeOH (10 mL) provided N-alkyl phthalimide. A second elution with ether (20 mL) gave a mixture of the fluorous phosphine oxide 4 and the fluorous hydrazine 9.

Example 7.1

N-Allyl phthalimide

CAS Registry Number [5428-09-1]; $^1$H NMR (CDCl$_3$) δ7.90–7.84 (m, 2H), 7.80–7.72 (m, 2H), 5.96–5.83 (m, 1H), δ5.29–δ5.19 (m, 2 H), δ4.32–4.3 (m, 2H); LRMS m/z (relative intensity) 187 (M$^+$, 100%), 169 (53%), 76 (68%).

Example 7.2

N-(p-Fluorobenzyl) phthalimide $^1$H NMR δ7.87–7.84 (m 2H), δ7.74–7.70 (m, 2H), δ7.46–7.40 (m, 2H), δ7.04–6.96 (m, 2H), 4.82 (s, 2H); $^{19}$F NMR (CDCl$_3$) −113.1; LRMS m/z (relative intensity) 255 (M$^+$, 100%), 237 (29%), 122 (63%), 76 (34%).

Example 8

General procedure for Mitsunobu reactions of N-(t-butoxycarbonyl)-p-toluene sulfonamide promoted by fluorous phosphine 3 and fluorous DEAD 10 (procedure C)

A solution of fluorous DEAD 10 (85 mg, 0.105 mmol) in THF (0.5 mL) was added to a solution of fluorous phosphine 3 (100 mg, 0.105 mmol) in THF (0.5 mL) at 0° C. Alcohol (0.105 mmol) was added neat followed by a solution of N-(t-butoxycarbonyl)-p-toluene sulfonamide (19 mg, 0.07 mmol) in THF (0.5 mL). After stirring at room temperature for 3 h the solvent was evaporated from the reaction mixture and the residue was loaded onto 2 g of FRPS using methanol. Elution with 80% MeOH/H$_2$O (10 mL) gave N-alkyl-N-(t-butoxycarbonyl)-p-toluene sulfonamide. A second elution with ether was done to collect a mixture of the fluorous phosphine oxide 4 and the fluorous hydrazine 9.

Example 8.1

N-Methyl -N-(t-butoxycarbonyl)-p-toluene sulfonamide $^1$H NMR δ7.78 (d, 8.2 Hz, 2H), δ7.32 (d, 8.1 Hz, 2H), δ3.36 (s, 3H), δ2.45 (s, 3H), δ1.36 (s, 3H); LRMS m/z (relative intensity) 185 (22%), 155 (18%), 91 (100%), 65 (32%)

Example 8.2

N-Allyl-N-(t-butoxycarbonyl)-p-toluene sulfonamide $^1$H NMR (CDCl$_3$) δ7.81–7.79 (m, 2H), δ7.32–7.29 (m, 2H), δ6.00–5.88 (m, 1H), δ5.37–5.29 (m, 1H), δ5.27–5.22 (m, 1H) 4.48–4.44 (m, 2H); LRMS m/z (relative intensity) 210 (2%), 155 (17%), 91 (100%).

Example 8.3

N-(p-fluorobenzyl)-N-(t-butoxycarbonyl)-p-toluene sulfonamide $^1$H NMR δ7.58–7.56 (m, 2H), δ7.45–7.41 (m, 2H), δ7.26–7.23 (m, 2H) δ7.07–7.00 (m, 2H), 5.00 (s, 2H), δ2.42 (s, 3H), δ1.32 (s, 9H); LRMS m/z (relative intensity) 281 (2%), 206 (48%), 124 (80%), 91 (100%).

Mitsunobu reactions of 4-(4-nitrophenyl)butyric acid promoted by fluorous phosphine 3 and fluorous DEAD 10 were done using Procedure C (see above).

Example 8.4

Methyl 4-(4-nitrophenyl)butyrate $^1$H NMR (CDCl$_3$) δ8.16 (d, J=8.6 Hz, 2H), 7.35 (d, J=8.6 Hz, 2H), 3.69 (s, 3H), 2.77 (t, J=7.7 Hz, 2H), 2.36 (t, J=7.3 Hz, 2H), 1.99 (m, 2H); LRMS m/z (relative intensity) 223 (M$^+$, 66%), 192 (33%), 150 (76%), 74 (100%), 59(15%).

Example 8.5

Allyl 4-(4-nitrophenyl)butyrate $^1$H NMR (CDCl$_3$) δ8.16 (d, J=8.7 Hz, 2H), δ7.35 (d, J=8.6 Hz, 2H), δ5.99–5.86 (m, 1H), δ5.36 −5.29 (m, 1H), δ5.28–5.23 (m, 1H), δ4.60–4.58 (mn, 2H), δ2.78 (t, J=7.7 Hz, 2H), δ2.39 (t, J=7.3 Hz, 2H), δ2.05–1.96 (in, 2H); LRMS m/z (relative intensity) 249 (M$^+$ 53%), 208 (100%), 116 (76%).

Example 8.6 p-Flurobenzyl 4-(4-nitrophenyl)butyrate $^1$H NMR (CDCl$_3$) δ8.18–8.13 (m, 2H), δ7.37 7–7.27 (m, 4H), δ7.08–6.99 (m, 2H), δ5.09 (s, 2H), δ2.76 (t, J=7.6 Hz, 2H), δ2.39 (t, J=7.4 Hz, 2H), δ2.05–1.95 (m, 2H); $^{19}$F NMR (CDCl$_3$) δ–112; LRMS m/z (relative intensity) 317 (26%), 208 (9%), 109 (100%).

Example 9

4,4,5,5,6,6,7,7,8,8,9,9,9-Tridecafluorononan-1-ol (20)

2-iodo-4,4,5,5,6,6,7,7,8,8,9,9,9-tridecafluorononan-1-ol 19 (15 g, 29.8 mmol) was slowly added to a solution of lithium aluminum hydride (1.14 g, 30.1 mmol) in THF (60 mL). After stirring at room temperature overnight, the reaction mixture was quenched with ethylacetate (5 mL). Water (150 mL) was added to the mixture and extracted with ether (3×75 mL). Ether layers were combined, washed with water and brine solution. The ether layer was then concentrated and distilled to get 20 (8.66 g, 77%) bp 90–92° C. at aspirator pressure; $^1$H NMR (CDCl$_3$) δ3.75 (t, J=6.1 Hz, 2H), δ2.31–2.13 (mn, 2H), δ1.92–1.83 (mn, 2H)

Example 10

Bis(3,3,4,4,5,5,6,6,7,7,8,8,8-tridecalfluorooctyl) hydrazine dicarboxylate (21)

This compound was synthesized similar to 9. mp 98–99° C.; $^1$H NMR (acetone-d$^6$) δ8.31 (b, 2H), 4.19 (t, J=6.2 Hz, 4H), δ2.41–2.23 (m, 4H), δ1.98–1.89 (m, 2H); $^{13}$C NMR (acetone-d$^6$) δ157.9, δ125–110 (m), δ64.9, δ28.5 (t, J=88.3 Hz), δ21.5; $^{19}$F NMR –80.6 (3H), –113.8 (2H), –121.4 (2H), –122.4 (2H), –122.9 (2H), –125.7 (2H); HRMS calculated 840.0555 found 840.0555; IR (thin film) 1741 cm$^{-1}$, 3271 cm$^{-1}$.

Example 10.1

Bis(3,3,4,4,5,5,6,6,7,7,8,8,8-tridecafluorooctyl)diazo dicarboxylate (22)

This compound was synthesized similar to 10. mp 51–52° C.; $^1$H NMR (acetone-d$^6$) δ4.66 (t, J=6.1 Hz, 4H), δ2.56–2.38 (m, 4H), δ2.25–2.16 (m, 4H); $^{13}$C NMR (acetone-d$^6$) δ161.3, δ124.2–105.3 (m), δ68.9, δ28.2 (t, J=88 Hz), δ20.7; $^{19}$F NMR (acetone-d$^6$) δ–79.6 (6F), –113.3 (4F), δ–120.8 (4F), δ121.7 (4F), –122.3 (4F), –125 (4F); LRMS 840 (M$^+$+2, 6%), 463 (6%), 436 (15%), 341 (32%), 295 (25%), 91 (100%); IR (thin film) 1783 cm$^{-1}$.

Example 11

1-Bromo-4-(3,3,4,4,5,5,6,6,7,7,8,8,9,9,10,10,10-heptadecafluorooctyl)benzene

Zinc powder (3.24 g, 52.3 mmol) was placed in a 250 mL round bottom flask equipped with a dropping funnel and a condenser. Zn was dried under vacuum and cooled under Argon. Freshly distilled THF (8 mL) was added at room temperature and the mixture was stirred for 5 min. 1,2-Dibromoethane (0.2 mL) was added at 65° C. and the reaction flask was maintained at this temperature for 2 min and then cooled to room temperature. Chlorotrimethylsilane (0.2 mL) was added at room temperature. After 20 min, a solution of 1,1,1,2,2,3,3,4,4,5,5,6,6,7,7,8,8-heptadecafluoro-8-iodooctane (25 g, 43.6 mmol) in THF (44 mL) was added dropwise. The rate of addition was adjusted such that the reaction mixture was maintained at room temperature. After 24 h at room temperature, the colorless organozinc was cannulated to a 250 mL round bottom flask equipped with a condenser and charged with 1-bromo-4-iodobenzene (12.7 g, 44.9 mmol), tetrakis(triphenylphosphine) palladium(0) (1.51 g, 1.31 mmol) in THF (22 mL). The reaction mixture was stirred at 45° C. for 24 h. The solvent was then removed under reduced pressure; the crude residue was dissolved in methylene chloride (50 mL) and was extracted with FC-72 (7×50 mL). The FC-72 layers were combined and the solvent was evaporated. The crude product obtained was then distilled under low pressure to give (13.4 g, 51%) as a colorless oil: bp 123° C./0.4 Torr; $^1$H NMR (CDCl$_3$) δ7.48–7.43 (m, 2H), δ7.13–7.09 (m, 2H), δ2.91–2.85 (m, 2H), δ2.45–2.27 (m, 2H).

Example 12

Bis-phenyl-[4-(3,3,4,4,5,5,6,6,7,7,8,8,9,9,10,10,10-heptadecafluorooctyl)phenyl]phosphane A solution of t-BuLi (1.7 M in pentane, 1.95 mL, 3.32 mmol) was added slowly to 1-bromo-4-(3,3,4,4,5,5,6,6,7,7,8,8,9,9,10,10,10-tridecafluoro-octyl)benzene (1 g, 1.66 mmol) in ether (130 mL) at –78° C. After 1 h at –78° C. for, chlorodiphenylphosphine (0.36 ml, 1.99 mmol) was added; the reaction mixture was warmed to room temperature and stirred overnight. Then the reaction mixture was quenched with water (10 mL). The ether layer was separated. The aqueous layer was further extracted with ether (3×10 mL). The ether layers were then combined, dried with magnesium sulfate and concentrated under reduced pressure. The residue was then purified by column chromatography on silica gel. Elution with 20:1 hexane:ethylacetate gave bis-phenyl-[4-(3,3,4,4,5,5,6,6,7,7,8,8,9,9,10,10,10-heptadecafluorooctyl)phenyl]phosphane (970 mg, 81%) as colorless oil; $^1$H NMR (CDCl$_3$) δ7.37–7.21 (m, 14H), δ2.99–2.93 (m, 2H), δ2.45–2.33 (m, 2H); $^{31}$P NMR (CDCl$_3$) δ–4.84. The retention time of this phosphine was 25 min on a Fluofix column under the standard conditions.

Example 12.1

Mitsunobu reaction of 4-(4-nitrophenyl)butyric acid and methanol promoted by bis-phenyl-[4-(3,3,4,4,5,5,6,6,7,7,8,8,9,9,10,10,10-heptadecafluorooctyl)phenyl]phosphane and fluorous DEAD 10 was done using Procedure C (see above) to afford the pure substitution product.

Although the present invention has been described in detail in connection with the above examples, it is to be understood that such detail is solely for that purpose and that variations can be made by those skilled in the art without departing from the spirit of the invention except as it may be limited by the following claims.

What is claimed is:

1. A method of effecting a nucleophilic substitution of an alcohol to produce a target product comprising the step:
    reacting the alcohol and a nucleophile with an azodicarboxylate and a phosphine, at least one of the azodicarboxylate and the phosphine including at least one fluorous tag.

2. The method of claim 1 wherein the azodicarboxylate includes at least one fluorous tag and the phosphine includes at least one fluorous tag.

3. The method of claim 2 further including the step of separating the target product from at least one of the fluorous tagged azodicarboxylate and the fluorous tagged phosphine via a fluorous separation technique.

4. The method of claim 3 wherein the fluorous separation technique is liquid-liquid extraction.

5. The method of claim 3 wherein the fluorous separation technique is solid-liquid extraction.

6. The method of claim 3 wherein the fluorous separation technique is fluorous solid phase extraction.

7. The method of claim 2 wherein the fluorous tagged azodicarboxylate has the formula

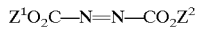

wherein $Z^1$ is

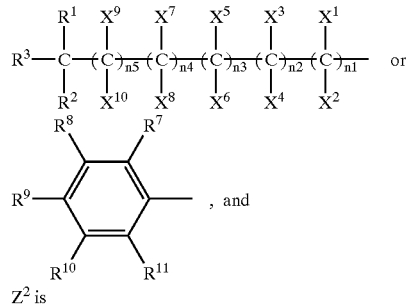

$Z^2$ is

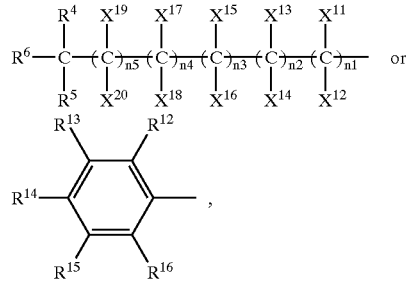

wherein n1, n2, n3, n4, n5, n6, n7, n8, n9 and n10 are independently 1 or 0, wherein $X^1, X^2, X^3, X^4, X^5, X^6, X^7, X^8, X^9, X^{10}, X^{11}, X^{12}, X^{13}, X^{14}, X^{15}, X^{16}, X^{17}, X^{18}, X^{19}$ and $X^{20}$ are independently H, F, Cl, an alkyl group, an aryl group or an alkoxy group, and wherein $R^1, R^2, R^3, R^4, R^5, R^6, R^7, R^8, R^9, R^{10}, R^{11}, R^{12}, R^{13}, R^{14}, R^{15}$ or $R^{16}$ are independently H, F, Cl, an alkyl group, an alkoxy group, a thioalkyl group, a dialkylamino group, a nitro group, a cyano group, a perfluoroalkyl group, a hydrofluoroalkyl group, a fluorinated ether group, a fluorinated amine group, O—$Rf^1$, S—$Rf^2$, or —N($Rf^3$)($R^{22}$), wherein $R^{22}$ is an alkyl group or $Rf^4$ wherein $Rf^1, Rf^2, Rf^3$ and $Rf^4$ are independently a fluorous group selected from, the group of a perfluoroalkyl group, a hydrofluoroalkyl group, a fluorinated ether group or afluorinated amine group, at least one of $R^1, R^2, R^3, R^4, R^5, R^6, R^7, R^8, R^9, R^{10}, R^{11}, R^{12}, R^{13}, R^{14}, R^{15}$ or $R^{16}$ being O—$Rf^1$, S—$Rf^2$, —N($Rf^3$)($R^{22}$), a perfluoroalkyl group, a hydrofluoroalkyl group, a fluorinated ether group or a fluorinated amine group.

8. The method of claim 7 wherein linear perfluoroalkyl groups are of 3 to 20 carbons and hydrofluoroalkyl groups are of 3 to 20 carbons, hydrofluoroalkyl groups comprising up to one hydrogen atom for each two fluorine atoms.

9. The method of claim 2 wherein the fluorous tagged phosphine has the formula

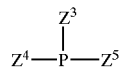

wherein $Z^3$ is

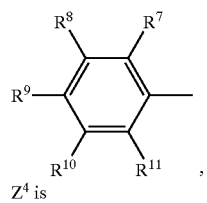

$Z^4$ is

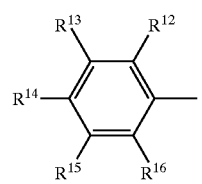

and $Z^5$ is

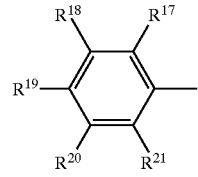

wherein $R^7, R^8, R^9, R^{10}, R^{11}, R^{12}, R^{13}, R^{14}, R^{15}, R^{16}, R^{17}, R^{18}, R^{19}, R^{20}$, and $R^{21}$ are independently H, F, Cl, an alkyl group, an alkoxy group, a thioalkyl group, a dialkylamino group, a nitro group, a cyano group, a perfluoroalkyl group, a hydrofluoroalkyl group, a fluorinated ether group, a fluorinated amine group, O—$Rf^{1}$, S—$Rf^{2}$, —N($Rf^3$)($R^{22}$), wherein $R^{22}$ is an alklyl group or $Rf^4$ wherein $Rf^1, R^2, Rf^3$ and $Rf^4$ are independently a fluorous group selected from the group of a perfluoroalkyl group, a hydrofluoroalkyl group, a fluorinated ether group or a fluorinated amine group, at least one of $R^7, R^8, R^9, R^{10}, R^{11}, R^{12}, R^{13}, R^{14}, R^{15}, R^{16}, R^{17}, R^{18}, R^{19}, R^{20}$ and $R^{21}$ being O—$Rf^1$, S—$Rf^2$, —N($Rf^3$)($R^{22}$), perfluoroalkyl group, a hydrofluoroalkyl group, a fluorinated ether group or a fluorinated amine group.

10. The method of claim 9 wherein linear perfluoroalkyl groups are of 3 to 20 carbons and hydrofluoroalkyl groups are of 3 to 20 carbons, hydrofluoroalkyl groups comprising up to one hydrogen atom for each two fluorine atoms.

11. The method of claim 1 wherein the alcohol is a primary alcohol or a secondary alcohol.

12. The method of claim 2 wherein the alcohol and the nucleophile are added to a mixture of the fluorous tagged azodicarboxylate and the fluorous tagged phosphine.

13. The method of claim 2 wherein the fluorous tagged azodicarboxylate has the formula

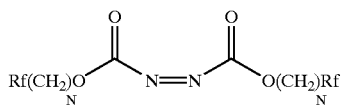

wherein N is an integer between 1 and 5 and Rf is a perfluoroalkyl group.

14. The method of claim 13 wherein the perfluoroalkyl group is of 3 to 20 carbons.

15. A compound having the formula

wherein $Z^1$ is wherein $Z^1$ is

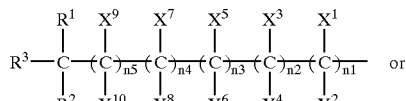

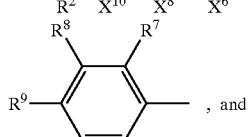

$Z^2$ is

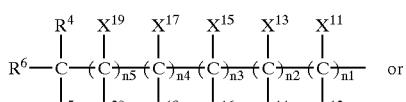

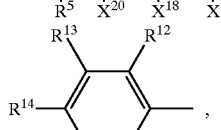

wherein n1, n2, n3, n4, n5, n6, n7, n8, n9 and n10 are independently 1 or 0, wherein $X^1$, $X^2$, $X^3$, $X^4$, $X^5$, $X^6$, $X^7$, $X^8$, $X^9$, $X^{10}$, $X^{11}$, $X^{12}$, $X^{13}$, $X^{14}$, $X^{15}$, $X^{16}$, $X^{17}$, $X^{18}$, $X^{19}$ and $X^{20}$ are independently H, F, Cl, an alkyl group, an aryl group or an alkoxy group, and wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$ and $R^{16}$ are independently H, F, Cl, an alkyl group, an alkoxy group, a thioalkyl group, a dialkylamino group, a nitro group, a cyano group, a perfluoroalkyl group, a hydrofluoroalkyl group, a fluorinated ether group, a fluorinated amine group, O—$Rf^1$, S—$Rf^2$, —N($Rf^3$)($R^{22}$), wherein $R^{22}$ is an alkyl group or $Rf^4$ wherein $Rf^1$, $Rf^2$, $Rf^3$ and Rf4 are independently a fluorous group selected from the group of a perfluoroalkyl group, a hydrofluoroalkyl group, a fluorinated ether group or a fluorinated amine group, at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$ or $R^{16}$ being O—$Rf^1$, S—$Rf^2$, —N($Rf^3$)($R^{22}$), a perfluoroalkyl group, a hydrofluoroalkyl group, a fluorinated ether group or a fluorinated amine group.

16. The compound of claim 15 wherein $Z^1$ and $Z^2$ are $Rf(CH_2)_N$—, wherein N is an integer in the range of 1 to 5 and Rf is a perfluoroalkyl group.

17. The compound of claim 16 wherein the perfluoroalkyl group is of 3 to 20 carbons.

18. A compound having the formula

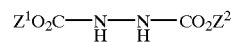

wherein $Z^1$ is wherein $Z^1$ is

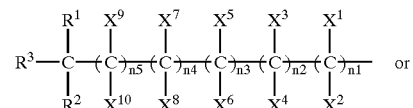

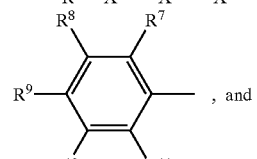

$Z^2$ is

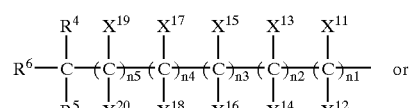

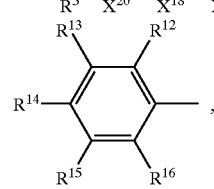

wherein n1, n2, n3, n4, n5, n6, n7, n8, n9 and n10 are independently 1 or 0, wherein $X^1$, $X^2$, $X^3$, $X^4$, $X^5$, $X^6$, $X^7$, $X^8$, $X^9$, $X^{10}$, $X^{11}$, $X^{12}$, $X^{13}$, $X^{14}$, $X^{15}$, $X^{16}$, $X^{17}$, $X^{18}$, $X^{19}$ and $X^{20}$ are independently H, F, Cl, an alkyl group, an aryl group or an alkoxy group, and wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$ and $R^{16}$ are independently H, F, Cl, an alkyl group, an alkoxy group, a thioalkyl group, a dialkylamino group, a nitro group, a cyano group, a perfluoroalkyl group, a hydrofluoroalkyl group, a fluorinated ether group, a fluorinated amine group, O—$Rf^1$, S—$Rf^2$, —N($Rf^3$) ($R^{22}$), wherein $R^{22}$ is an alklyl group or $Rf^4$ wherein $Rf^1$, $Rf^2$, $Rf^3$ and $Rf^4$ are independently a fluorous group selected from the group of a perfluoroalkyl group, a hydrofluoroalkyl group, a fluorinated ether group or a fluorinated amine group, at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$ or $R^{16}$ being O—$Rf^1$, S—$Rf^2$, —N($Rf^3$)($R^{22}$), a perfluoroalkyl group, a hydrofluoroalkyl group, a fluorinated ether group or a fluorinated amine group.

19. The compound of claim 18 wherein $Z^1$ and $Z^2$ are $Rf(CH_2)_N$—, wherein N is an integer in the range of 1 to 5 and Rf is a perfluoroalkyl group.

20. The compound of claim 19 wherein the perfluoroalkyl group is of 3 to 20 carbons.

21. A method of synthesizing a compound having the formula:

comprising the step reacting a compound having the formula:

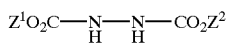

with an oxidant, wherein $Z^1$ is

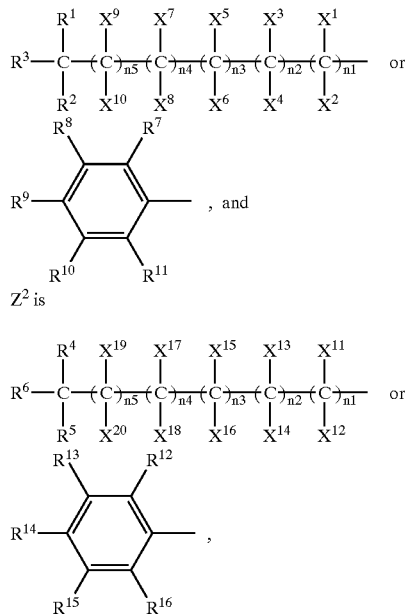

$Z^2$ is wherein n1, n2, n3, n4, n5, n6, n7, n8, n9 and n10 independently 1 or 0, wherein $X^1$, $X^2$, $X^3$, $X^4$, $X^5$, $X^6$, $X^7$, $X^8$, $X^9$, $X^{10}$, $X^{11}$, $X^{12}$, $X^{13}$, $X^{14}$, $X^{15}$, $X^{16}$, $X^{17}$, $X^{18}$, $X^{19}$ and $X^{20}$ are independently H, F, Cl, an alkyl group, an aryl group or an alkoxy group, and wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$ and $R^{16}$ are independently H, F, Cl, an alkyl group, an alkoxy group, a thioalkyl group, a dialkylamino group, a nitro group, a cyano group, a perfluoroalkyl group, a hydrofluoroalkyl group, a fluorinated ether group, a fluorinated amine group, O—$Rf^1$, S—$Rf^2$, —N($Rf^3$)($R^{22}$), wherein $R^{22}$ is an alklyl group or $Rf^4$ wherein $Rf^1$, $Rf^2$, $Rf^3$ and $Rf^4$ are independently a fluorous group selected from the group of a perfluoroalkyl group, a hydrofluoroalkyl group, a fluorinated ether group or a fluorinated amine group, at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$ or $R^{16}$ being O—$Rf^1$, S—$Rf^2$, —N($Rf^3$)($R^{22}$), a perfluoroalkyl group, a hydrofluoroalkyl group, a fluorinated ether group or a fluorinated amine group.

22. The method of claim 21 wherein the oxidant is dibromine or N-bromosuccinimide.

23. The method of claim 21 wherein $Z^1$ and $Z^2$ are $Rf(CH_2)_N$—, wherein N is an integer in the range of 1 to 5 and Rf is a perfluoroalkyl group.

24. The method of claim 23 wherein the perfluoroalkyl group is of 3 to 20 carbons.

\* \* \* \* \*